(12) United States Patent
Aboussou et al.

(10) Patent No.: US 11,442,053 B2
(45) Date of Patent: Sep. 13, 2022

(54) PROCESS FOR QUANTIFYING THE PYRITIC SULFUR AND THE ORGANIC SULFUR OF A ROCK SAMPLE

(71) Applicant: IFP Energies nouvelles, Rueil-Malmaison (FR)

(72) Inventors: Anabel Aboussou, Rueil-Malmaison (FR); Violaine Lamoureux-Var, Rueil-Malmaison (FR); Daniel Pillot, Rueil-Malmaison (FR); Isabelle Kowalewski, Rueil-Malmaison (FR); Bruno Garcia, Rueil-Malmaison (FR); Thomas Wagner, Edinburgh (GB); Christian März, Leeds (GB)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 656 days.

(21) Appl. No.: 16/457,216

(22) Filed: Jun. 28, 2019

(65) Prior Publication Data
US 2020/0003750 A1 Jan. 2, 2020

(30) Foreign Application Priority Data

Jun. 29, 2018 (FR) .................... 18/56.042

(51) Int. Cl.
*G01N 33/24* (2006.01)
*E21B 49/02* (2006.01)
*G01N 25/00* (2006.01)

(52) U.S. Cl.
CPC ........... *G01N 33/241* (2013.01); *E21B 49/02* (2013.01); *G01N 25/00* (2013.01)

(58) Field of Classification Search
CPC ...... G01N 33/241; G01N 25/00; G01N 33/24; E21B 49/02
See application file for complete search history.

(56) References Cited

U.S. PATENT DOCUMENTS 8,796,035 B2 8/2014 Espitalie et al.
10,895,567 B2 * 1/2021 Aboussou .............. G01N 33/24
(Continued)

FOREIGN PATENT DOCUMENTS

| EP | 2 342 557 A1 | 7/2011 |
| FR | 2937737 A1 | 4/2010 |
| FR | 3072173 A1 | 4/2019 |

OTHER PUBLICATIONS

Preliminary Search Report for FR 18/56.042, dated Apr. 1, 2019.
(Continued)

*Primary Examiner* — Catherine T. Rastovski
*Assistant Examiner* — Kaleria Knox
(74) *Attorney, Agent, or Firm* — Fitch, Even, Tabin & Flannery LLP

(57) ABSTRACT

A rock sample is subjected to a heating sequence in an inert atmosphere, the effluents resulting from this heating are oxidized, the hydrocarbon-based compounds, the CO, the $CO_2$ and the $SO_2$ released are measured, and a pyrolysis pyritic sulfur content is deduced therefrom. The residue resulting from the heating in an inert atmosphere is then heated in an oxidizing atmosphere and the CO and the $CO_2$ released are measured. The pyritic sulfur content is determined at least from the pyrolysis pyritic sulfur content and from a parameter which is a function of the hydrogen content and of the oxygen content of the organic matter of the sample. It is also possible to determine the organic sulfur content from the pyritic sulfur content and from a measurement of the $SO_2$ during the heating sequence in an oxidizing atmosphere.

19 Claims, 7 Drawing Sheets

(56) References Cited

U.S. PATENT DOCUMENTS

2011/0263034 A1  10/2011  Espitalie et al.
2019/0107522 A1   4/2019  Romero-Sarmiento et al.

OTHER PUBLICATIONS

Lorant F et al: "Characterization of sulfur in reservoir rocks by rock-eval analysis", 13th European Symposium on Improved Oil Recovery 2005—2005 European Association of Geoscientists and Engin,, 2005, pp. 1-8, XP009178226.

* cited by examiner

PROCESS FOR QUANTIFYING THE PYRITIC SULFUR AND THE ORGANIC SULFUR OF A ROCK SAMPLE

BACKGROUND OF THE INVENTION

Field of the Invention

CROSS REFERENCE TO RELATED APPLICATION

Reference is made to French Patent Application No. 18/56.042 filed Jun. 29, 2018, to which priority is claimed and which is incorporated herein by reference in its entirety.

The present invention relates to the technical field of the oil industry, and more particularly the field of the exploration and exploitation of a geological formation in which hydrocarbons are trapped.

More specifically, the present invention relates to the characterization and the quantification of the sulfur present within a sedimentary rock, such as a marine clay rich in organic matter.

Description of the Prior Art

In order to meet the increasing energy demand, the oil industry is increasingly turning to the production of unconventional crude oils, which are richer in sulfur than conventional oils. However, the sulfur content of an unconventional crude oil, and also the type of sulfur-containing organic compounds that it contains, are key parameters of the quality of this oil and of the refining products which are derived therefrom. Furthermore, the regulations impose increasingly lower sulfur contents for products derived from refining. For these reasons, it is important to know how to precisely characterize and quantify the sulfur present in the rocks which are the source of these sulfur-containing crude oils.

In the case of oil source rocks, the main two sulfur-containing compounds are organic sulfur and pyritic sulfur. The quantification of the organic sulfur, independently of the pyritic sulfur, is of great importance in oil exploration, since it makes it possible to know exactly the amount of sulfur associated with the organic matter of the source rocks, which is the source of the sulfur present in the oil generated by these source rocks. In particular, the distinct quantification of the pyritic sulfur and of the organic sulfur makes it possible to:

characterize the type of organic matter of the source rock and predict the quality of the oil generated by the source rock with regard to its sulfur content-. Indeed, the characterization of the type of organic matter of the source rocks is conventionally carried out as a function of the elemental content of this organic matter with respect to carbon (C), to hydrogen (H) and to oxygen (O). This conventional characterization of the type of organic matter is carried out by the conventional Van Krevelen diagram, which represents the hydrogen/carbon (H/C) atomic ratio, as a function of the oxygen/carbon (O/C) atomic ratio. Since the potential of an organic matter to generate oil depends on its H, C and O composition, this diagram makes it possible to distinguish three types of organic matter according to their oil potential. Indeed, this diagram can be correlated to the origin and the deposition environment of the organic matter. Conventionally, organic matter of lacustrine type (type I), marine type (type II) and terrestrial type (type Ill) are distinguished. The quantification of the sulfur of the organic matter independently of the pyrite sulfur (or pyritic sulfur) provides an additional parameter which enables a finer characterization of the type of organic matter and thus a finer characterization of its deposition environment and of the type of oil that it can generate. This finer characterization is carried out with the expanded three-dimensional Van Krevelen diagram: H/C as a function of O/C and of $S^{org}/C$ where $S^{org}$ is the organic sulfur content. This expanded diagram makes it possible to distinguish more finely the various types of organic matter, in particular to identify the organic matters of IS and IIS type which have the same origins as the types I and II, but containing sulfur, and which are probably deposited in an anoxic or euxinic environment. This presence of sulfur also indicates that the oil resulting from the cracking of this organic matter will have a higher sulfur content. In general, the information on the type of organic matter of the source rock provides information on the potential of the source rock to generate oil and on the expected quality of this oil, in particular with regard to its sulfur content;

provide a parameter in addition to the oil-source rock correlation. Indeed, the oil-source rock correlation is a very important study which those skilled in the art must carry out in order to evaluate the oil system. It makes the connection between the oils contained in a reservoir and the source rock(s) which generated these oils. Knowing that the cracking of source rocks containing organic matter rich in sulfur results in the formation of oils and gases that are also rich in sulfur, a method for quantifying the sulfur of the organic matter, independently of the pyrite sulfur, thus provides a key parameter for the oil-source rock correlation.

PRIOR ART

The following documents will be cited in the rest of the description:

Acholla, F. V., Orr, W. L., 1993. Pyrite removal from kerogen without altering organic matter: The chromous chloride method. Energy Fuels 7, 406-410.

Behar, F., Beaumont, V., De B. Penteado, H. L., 2001. Rock-Eval 6 Technology: Performances and Developments. Oil & Gas Science and Technology—Rev. IFP 56, 111-134.

Bolin, T. B., 2010. Direct determination of pyrite content in Argonne premium coals by the use of sulfur X-ray near edge absorption spectroscopy (S-XANES). Energy and Fuels 24, 5479-5482.

Canfield, D. E., Raiswell, R., Westrich, J. T., Reaves, C. M., Berner, R. A., 1986. The use of chromium reduction in the analysis of reduced inorganic sulfur in sediments and shales. Chemical Geology 54, 149-155.

Landais, P., Michels, R., Benkhedda, Z., Kister, J., Dereppe, J.-M., 1991. Behavior of Oxidized Type II Kerogen during Artificial Maturation. Energy and Fuels 5, 860-866.

Orr W., 1986, "Kerogen/asphaltene/sulfur relationships in sulfur-rich Monterey oils", Org. Geochem. Vol. 10, pp. 499-516, 1986.

Vairavamurthy, M. A., Maletic, D., Wang, S., Manowitz, B., Eglinton, T., Lyons, T., 1997. Characterization of sulfur-containing functional groups in sedimentary humic substances by X-ray absorption near-edge structure spectroscopy. Energy and Fuels 11, 546-553.

Vandenbroucke, M., Largeau, C., 2007. Kerogen origin, evolution and structure. Organic Geochemistry 38, 719-833.

Laboratory methods for quantifying the pyritic sulfur distinctly from the organic sulfur are known, such as the following techniques:

Elemental analysis of the kerogens, as described in the document Vandenbroucke and Largeau, 2007. It is one of the methods most commonly routinely used in laboratories. It is carried out in 2 steps:

Isolation of the kerogen (or else isolation of the organic matter). The kerogen is isolated from the crude rock by use of a series of chemical attacks with hydrochloric and hydrofluoric acid aimed at destroying the mineral matrix, the carbonates and the silicates. The pyrite ($FeS_2$), other metal sulfides, and also certain minor oxides, including iron oxides, being resistant to these various chemical attacks, remain preserved in the organic residue obtained. Thus, a kerogen from which the mineral matrix has been removed but which still contains the pyrite is obtained.

Elemental analysis of the iron (by induction coupled plasma atomic emission spectroscopy, known as ICP-AES) and of the sulfur (by infrared analysis). The hypothesis put forward here is that the iron present in the kerogen obtained would only be in the form of pyrite ($FeS_2$). Consequently, starting from the measurement of the iron content (ICP-AES) of the kerogen, the pyrite content can be stoichiometrically calculated, making it possible to thus determine the pyritic sulfur content. Then, starting from the measurement of the sulfur content (IR) of the kerogen, it is possible to deduce therefrom the organic sulfur content by the difference between the total sulfur (measured by infrared) and the pyritic sulfur.

This first laboratory method according to the prior art has the following drawbacks:

length of the analysis time: approximately one week;

it requires preparation and chemical separation steps which are laborious and dangerous since they use strong acids;

it does not allow the measurements to be automated;

it is based on the hypothesis that all the iron contained in the organic matter is pyritic. However, if the iron contained in the organic matter is also in other forms such as oxides or sulfides other than $FeS_2$, then the pyritic sulfur content is overestimated and the organic sulfur content is underestimated.

Extraction of the pyrite using chromium II chloride and by elemental analysis of the starting rock, as described in the documents Canfield et al., 1986; Acholla et Orr, 1993. According to this approach, a chemical attack with hot hydrochloric acid (HCl) is carried out in a first step in order to extract all the volatile sulfur contained in rock samples. Once this step is carried out, the samples are then treated, under hot conditions, with a solution consisting of hydrochloric acid (HCl) and of chromium II chloride ($CrCl_2$) making it possible to extract the pyrite ($FeS_2$). The sulfur-containing effluent ($H_2S$), released by the reduction of the pyrite by this solution, passes into a trap composed of a solution of silver nitrate ($AgNO_3$), wherein it precipitates in the form of silver sulfide ($Ag_2S$). The $Ag_2S$ precipitate obtained is weighed, which makes it possible to stoichiometrically quantify the pyritic sulfur content, by assuming that the pyrite was entirely converted into silver sulfide. The organic sulfur content is then deduced by the difference between the total sulfur content, obtained by the elemental analysis of the starting rock, and the pyritic sulfur content. This method is based on the hypothesis that all the pyrite is reduced to $H_2S$.

This second laboratory method according to the prior art has the following drawbacks:

It requires preparation and chemical separation steps which are laborious and dangerous since they use strong acids;

It does not allow the measurements to be automated; and

It is based on the hypothesis that all the pyrite is reduced to $H_2S$. If a portion of the pyrite is not reduced, then the pyritic sulfur content is underestimated and the organic sulfur content is overestimated. In particular, pyrite-rich samples risk being in this category.

Sulfur X-ray absorption near edge structure (S-XANES) spectroscopy, as described in the documents Vairavamurthy et al., 1997; Bolin, 2010. According to this approach, the S-XANES provides information on the oxidation state of the sulfur-containing compounds. In a typical analysis, the spectrum of a sample is deconvoluted with various linear combinations of the spectra of various sulfur standards. The best adjustment is chosen so as to indicate the actual composition of the various sulfur-containing compounds of this sample. This technique thus makes it possible to quantitatively determine the pyritic sulfur, the organic sulfur and the sulfates. In the case of rock analysis, it should be noted that very fine grinding of the sample is often necessary in order to obtain the best quantification of the pyritic sulfur, the peak of which is attenuated in samples that have not been finely ground.

This third laboratory method according to the prior art has the following drawbacks:

it requires very fine grinding of the samples; and it requires access to a synchrotron, which is a very heavy and very expensive piece of equipment.

Patent EP 2 342 557 corresponding to U.S. Pat. No. 8,796,035, relates to a device and to a method for sulfur characterization and quantification in a sample of sedimentary rocks or of petroleum products, is also known. More specifically, the method described in this patent comprises the following steps:

The sample in question is heated in a pyrolysis oven in a non-oxidizing atmosphere;

A portion of the pyrolysis effluents is oxidized, and the amount of $SO_2$ contained in this portion of the oxidized effluents is continuously measured;

the pyrolysis residues are transferred into an oxidation furnace and the amount of $SO_2$ contained in the effluents resulting from the oxidation heating of the pyrolysis residue is continuously measured; and The sulfur content in the sample is deduced therefrom.

However, this method makes it possible to determine the content of total sulfur present in the sample being studied, but does not make it possible to separately quantify the pyritic sulfur and the organic sulfur. Indeed, this method makes it possible to quantify the total sulfur content of a rock sample, by the measurement of the sulfur-containing effluents released by this sample during pyrolysis then oxidation. Two profiles corresponding to the sulfur are thus obtained: the first during the pyrolysis phase, and the second during the oxidation phase. In terms of the pyrolysis sulfur signal, it is possible to discriminate between the organic sulfur and the mineral sulfur due to the pyrite, since they systematically form two sufficiently distinct peaks. However, upon oxidation, the signals of these two sulfur-containing compounds are mingled, which prevents speciation of the organic and pyritic sulfur. Furthermore, numerous chemical reactions occur in the rock during the actual analysis. If some involve the organic sulfur and/or the pyritic sulfur, then they are capable of modifying their signals, which adds a level of difficulty to the quantification of the organic sulfur and of the pyritic sulfur by means of the process as described in the abovementioned patent.

Patent application FR 17/59447 (filing number), which describes a process for quantifying pyritic sulfur in a sedimentary rock sample, is also known. More specifically, this process according to the prior art comprises at least the following steps:

A. the sample is heated in an inert atmosphere, between a first temperature of between 100° C. and 320° C. and a second temperature of between 600° C. and 700° C., while following a first temperature gradient of between 1° C./min and 30° C./min;

B. at least one portion of the effluents resulting from the heating of the sample in an inert atmosphere is continuously oxidized, a first amount of $SO_2$ released as a function of the time of the heating in an inert atmosphere is continuously measured, and at least one pyrolysis sulfur content $S_{Pyrol}$ and one pyrolysis pyritic sulfur content $S_{Pyrol}^{Pyrit}$ are determined from the first amount of $SO_2$;

C. the residue of the sample resulting from the heating in an inert atmosphere is heated in an oxidizing atmosphere between a third temperature of between 280° C. and 320° C. and a fourth temperature of greater than or equal to 800° C., while following a second temperature gradient of between 1° C./min and 30° C./min;

D. a second amount of $SO_2$ released as a function of the time of the heating in an oxidizing atmosphere is continuously measured, at least one oxidation sulfur content $S_{Oxy}$ is determined from the second amount of $SO_2$, and at least one total sulfur content $S_{Total}$ is determined by the sum of the pyrolysis sulfur content $S_{Pyrol}$ and of the oxidation sulfur content $S_{Oxy}$.

This process according to the prior art then provides for the determination of at least one pyritic sulfur content $S^{Pyrit}$ contained in the sample on the basis of a formula of the type:

$$S^{Pyrit} = p(\alpha,\beta,\gamma) \cdot S_{Pyrol}^{Pyrit},$$

wherein $p(\alpha,\beta,\gamma)$ is a weighting function dependent on a parameter $\alpha$ representing a proportion of the pyrolysis pyritic sulfur relative to the total sulfur, on a parameter $\beta$ representing an effect of the mineral matrix on the proportion, and on a parameter $\gamma$ representing an effect of the organic matrix on the proportion, the values of the parameters being predetermined.

Moreover, according to one preferred variant of this process according to the prior art, the weighting function $p(\alpha,\beta,\gamma)$ is written in the form:

$$p(\alpha, \beta, \gamma) = \frac{(1+\beta+\gamma)}{\alpha}$$

However, the values of the parameters $\alpha$, $\beta$, and $\gamma$ must be predefined, prior to the implementation of the process according to the invention. Patent application FR 17/59447 describes default values, including in particular values of the parameter $\gamma$ as a function of the type of organic matter presumed to be present in the sedimentary rock sample in question. Thus, according to one variant of the process according to the prior art, if the rock sample contains an organic matter of lacustrine and/or marine origin, 0 can be used as the value for the parameter $\gamma$. According to another variant of the process according to the prior art, if the rock sample contains an organic matter of terrestrial origin, the value of the parameter $\gamma$ can be chosen between 0.23 and 0.29, and is preferentially equal to 0.26.

Thus, the process according to the prior art describes a method for directly quantifying the parameter $\gamma$, by taking into account the standard types of organic matter, which are pure poles. However, it may for example prove to be the case that the rock sample to be analysed contains more complex types of organic matter, such as derived from the modification or the mixing of organic matters of standard type. Specifically, through modification processes, an organic matter of standard marine type may have the chemical signature of an organic matter of standard terrestrial type. Furthermore, most sedimentary formations contain mixtures of the various standard types of organic matter. In proximal marine environments for example, it is possible to find in the sediments a mixture of organic matter of terrestrial type and organic matter of marine type. In such cases, the value of the parameter $\gamma$ recommended by patent application FR 17/59447 would not be suitable for the sedimentary rock studied.

In addition, the preferred form of the process according to the prior art for the weighting function $p(\alpha,\beta,\gamma)$ which is written in the form:

$$p(\alpha, \beta, \gamma) = \frac{(1+\beta+\gamma)}{\alpha}$$

is an approximate formula. Indeed, as is demonstrated in the application example described below, this formula, while it gives satisfactory results for the quantification of the pyritic sulfur present in a rock sample, remains however imprecise.

SUMMARY OF THE INVENTION

The present invention aims to overcome these drawbacks. Thus, the present invention relates to a method for a very precise quantification of the pyritic sulfur contained in a sedimentary rock sample, in particular from measurements carried out on the rock sample itself for quantifying the effect of the organic matrix. Furthermore, the implementation of the process according to the invention is simple and rapid. The process according to the invention also makes it possible, in one of its variants, to quantify the organic sulfur present in the sample, in addition to the pyritic sulfur.

The invention relates to a process for quantifying the pyritic sulfur in a sedimentary rock sample, in which at least the following steps are applied:

A. the sample is heated in an inert atmosphere, between a first temperature of between 80° C. and 320° C. and a second temperature of between 600° C. and 700° C., while following a first temperature sequence, and an amount of hydrocarbon-based compounds, an amount of CO and an amount of $CO_2$ released during the first temperature sequence are continuously measured;

B. at least one portion of the effluents resulting from the heating of the sample in an inert atmosphere is continuously oxidized, an amount of $SO_2$ released by the oxidation of the effluents as a function of the time of the heating in an inert atmosphere is continuously measured, and at least one pyrolysis pyritic sulfur content $S_{Pyrol}^{Pyrit}$ is determined from the amount of $SO_2$; and C. the residue of the sample resulting from the heating in an inert atmosphere is heated in an oxidizing atmosphere between a third temperature of between 280° C. and 320° C. and a fourth temperature of greater than or equal to 800° C., while following a second temperature sequence, and an amount of CO and an amount of $CO_2$ released during the second temperature sequence are continuously measured;

characterized in that at least one pyritic sulfur content $S^{Pyrit}$ contained in the sample is determined based on a formula of the type:

$$S^{Pyrit} = S_{pyrol}^{Pyrit} * \frac{\left(1 + \frac{\beta}{1-\beta} + \frac{\gamma}{1-\gamma}\right)}{\alpha}$$

wherein α is a parameter representing a proportion of the pyrolysis pyritic sulfur relative to the total sulfur, β is a parameter representing an effect of the mineral matrix on the proportion, and γ is a parameter representing an effect of the organic matrix on the proportion, the values of the parameters a and p being predetermined, and the parameter γ being determined from a formula of the type:

$$\gamma = f(OI, HI)$$

wherein $f$ is a function of at least one oxygen index OI and of a hydrogen index HI, the hydrogen index HI is a function at least of the amount of hydrocarbon-based compounds measured during the heating in an inert atmosphere and the amounts of CO and of $CO_2$ measured during the first and second temperature sequences, and the oxygen index OI being a function at least of the amounts of CO and of $CO_2$ measured during the first and second temperature sequences.

According to one implementation of the invention, the function $f$ may be a linear combination of the oxygen index OI and of the hydrogen index HI which is expressed according to a formula of the type: $\gamma = a*OI + b*HI + c$, wherein a, b and c are predetermined constants.

Advantageously, the constant a may be between 0.28 and 0.46, and may preferentially be equal to 0.37.

Preferentially, the constant b may be between −0.007 and −0.005, and may preferentially be equal to −0.006.

Preferably, the constant c may be between 4.99 and 6.49, and may preferentially be equal to 5.74.

According to one implementation of the invention, it is possible to determine the hydrogen index HI according to a formula of the type:

$$HI = \frac{100*S2}{TOC},$$

wherein
S2 is an amount of hydrocarbon-based compounds which are cracked during the first temperature sequence, S2 being determined from the amount of hydrocarbon-based compounds released during the heating in an inert atmosphere;
TOC is a total organic carbon content of the sample which is written in the form TOC(wt %)=PC+RC, wherein PC is a pyrolysis organic carbon content of the sample determined from the measurements of CO and $CO_2$ released during the first temperature sequence, and wherein RC is a residual organic carbon content of the sample determined from the measurements of CO and of $CO_2$ released during the second temperature sequence.

According to one implementation of the invention, it is possible to determine the oxygen index OI according to a formula of the type:

$$OI = \left[\frac{100*S3CO_2}{TOC}\right],$$

wherein:
$S3CO_2$ is an amount of $CO_2$ measured between the first temperature of the first temperature sequence and a first intermediate temperature of the first temperature sequence of between 350° C. and 450° C., and preferentially equal to 400° C.;
TOC is a total organic carbon content of the sample and is written TOC(wt %)=PC+RC, wherein PC is an organic carbon content from pyrolysis of the sample determined from the measurements of CO and $CO_2$ released during the first temperature sequence, and wherein RC is a residual organic carbon content of the sample determined from the measurements of CO and of $CO_2$ released during the second temperature sequence.

According to one implementation of the invention, the pyrolysis organic carbon content PC of the sample can be determined according to a formula of the type:

$$PC(\text{wt \%}) = [Q*0.083] + \left[\left(S3CO + \frac{1}{2}S3'CO\right)*\frac{12}{280}\right] + \left[S3CO_2*\frac{12}{440}\right],$$

with
S3CO2 is an amount of $CO_2$ measured between the first temperature of the first temperature sequence and a first intermediate temperature of the first temperature sequence of between 350° C. and 450° C., and preferentially equal to 400° C.;
S3CO is an amount of CO measured between the first temperature of the first temperature sequence and a second intermediate temperature of the first temperature sequence of between 500 and 600° C., and preferentially equal to 550° C.;
S3'CO is an amount of CO measured between the second intermediate temperature of the first temperature sequence and the second temperature of the first temperature sequence.

According to one implementation of the invention, the residual organic carbon content RC of the sample can be determined according to a formula of the type:

$$RC(\text{wt \%}) = \left[S4CO_2*\frac{12}{440}\right] + \left[S4CO*\frac{12}{280}\right],$$

wherein S4CO and $S4CO_2$ correspond respectively to an amount of CO and of $CO_2$ measured between the third temperature of the second temperature sequence and an intermediate temperature of the second temperature sequence of between 600° C. and 700° C., and preferentially equal to 650° C.

According to a first alternative of the invention according to which the sample is of reservoir rock type, the first temperature may be between 100° C. and 200° C.

According to a second alternative of the invention according to which the sample is of conventional source rock or immature shale play type, the first temperature may be between 280° C. and 320° C.

According to a third alternative of the invention according to which the sample may be of oil-bearing or gas-bearing shale play type, the first temperature may be between 80° C. and 120° C.

According to one implementation of the invention, the parameter a may be between 0.40 and 0.46, and may preferentially be equal to 0.43.

According to one implementation of the invention according to which the rock sample is of clay type, the parameter β may be between 0.04 and 0.7, and may preferentially be equal to 0.38.

According to one implementation of the invention according to which the rock sample is of marl type, and for which the parameter β may be between 0.7 and 0.9, and may preferentially be equal to 0.78.

According to one implementation of the invention according to which the rock sample is of limestone type, and for which the parameter β may be between 0.85 and 0.97, and may preferentially be equal to 0.9.

According to one variant of implementation of the invention, it is also possible to measure an amount of $SO_2$ released during the second temperature sequence, it is possible to determine at least one pyrolysis sulfur content $S_{Pyrol}$ from the amount of $SO_2$ measured during the first temperature sequence and an oxidation sulfur content $S_{Oxy}$ from the amount of $SO_2$ measured during the second temperature sequence, and it is possible to determine an organic sulfur content $S^{Org}$ from at least the pyritic sulfur content $S^{Pyrit}$, from the pyrolysis sulfur content $S_{Pyrol}$ and from the oxidation sulfur content $S_{Oxy}$.

According to one implementation of the invention according to which the fourth temperature is between 800° C. and 900° C., it is possible to determine an organic sulfur content $S^{org}$ according to the formula: $S_{Org} = S_{Pyrol} + S_{Oxy} - S^{Pyrit}$.

According to one alternative implementation of the invention according to which the fourth temperature is greater than 1150° C., and is preferentially less than 1250° C., it is possible to also determine a sulfate sulfur content $S_{Oxy}^{Sulfa}$ from the amount of $SO_2$ measured during the second temperature sequence, and it is possible to deduce an organic sulfur content therefrom according to the formula: $S^{Org} = S_{Pyrol} + S_{Oxy} - S^{Pyrit} - S_{Oxy}^{Sulfa}$.

Other features and advantages of the method according to the invention will become apparent upon reading the following description of nonlimiting exemplary embodiments with reference to the appended figures described hereinbelow.

DETAILED DESCRIPTION OF THE INVENTION

Figure 1A:
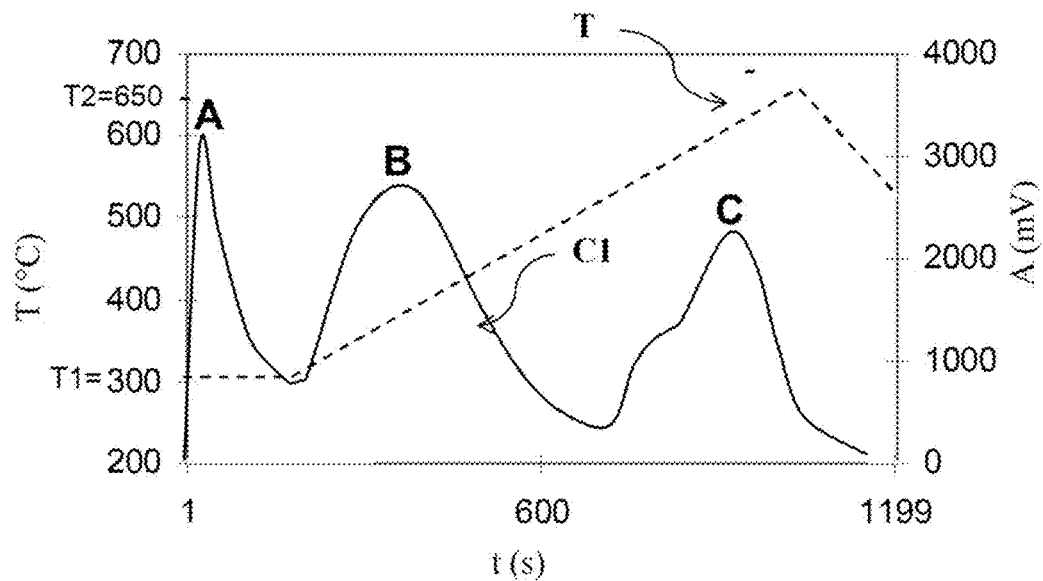
FIG. 1a presents an example of a measurement carried out by an $SO_2$ detector during a heating sequence under an inert atmosphere to which a rock sample is subjected.

In general, one of the subjects of the invention relates to a process for precisely quantifying the pyritic sulfur present in a sedimentary rock sample. In particular, the present invention makes it possible to quantify the pyritic sulfur distinctly from the organic sulfur. Advantageously, the process according to the invention makes it possible to quantify the organic sulfur present in a sedimentary rock sample, in addition to the pyritic sulfur.

The present invention can apply to sedimentary rocks of any type, containing pyrite and/or sulfur-containing organic matter. In particular, the present invention is suitable for samples of source rocks, of reservoir rocks or of shale play.

In general, the rock sample may for example have been taken by core drillings within an underground formation of interest or else result from rock cuttings derived from drilling. Advantageously, the sample as taken can be prepared (by washing, sieving, sorting, etc.) in order to remove the impurities (drilling sludge for example, pollutants, etc.) therefrom, and is then ground by hand or with a mechanical grinder.

The process according to the invention can be advantageously, but not in a limiting manner, carried out by use of the Rock-Eval® device (IFP Energies nouvelles, France), as described in particular in patent EP 2 342 557, corresponding to U.S. Pat. No. 8,796,035.

The process according to the invention comprises at least the following steps:
1. Heating sequence under an inert atmosphere (pyrolysis).
2. Heating sequence under an oxidizing atmosphere (oxidation).
3. Quantification of the pyritic sulfur.

According to a first variant, the process according to the invention can also comprise, at the outcome of step 3, a fourth step of quantifying the organic sulfur.

According to a second variant, the process can also comprise a step of calibrating one or more parameters required for carrying out step 3 below. This calibration step can equally be carried out prior to step 1 or prior to step 2 or prior to step 3 or else in parallel with one of these steps 1 or 2.

Steps 1 to 3 of the process according to the invention are described below, as are the first and second variants of the process according to the invention.

1. Heating Sequence Under an Inert Atmosphere (Pyrolysis)

During this step, the sedimentary rock sample in question is heated under an inert atmosphere (for instance under a nitrogen or helium stream) according to a program of predefined temperatures, variable overtime (substep 1.1 below). Simultaneously, at least one portion of the effluents resulting from this heating in an inert atmosphere is continuously oxidized (substep 1.2 below).

1.1. Heating in an Inert Atmosphere

According to the invention, the sample is heated by pyrolysis between a temperature T1 of between 80° C. and 320° C., and a temperature T2 of between 600° C. and 700° C., preferentially 650° C., according to a predetermined temperature sequence.

According to one implementation of the invention, the temperature sequence for the heating in an inert atmosphere may use a temperature gradient (or heating rate) of between 0.1° C./min and 30° C./min, preferentially between 20° C./min and 30° C./min, and very preferentially equal to 25° C./min. According to another implementation of the invention, the temperature sequence for the heating in an inert atmosphere may comprise at least one stationary temperature phase (during which the temperature is kept constant) and at least one temperature gradient (or heating rate), with it being possible for this gradient to be placed before or after the at least one stationary phase.

According to one implementation of the invention according to which the sample analysed is a reservoir rock, the temperature T1 is between 100° and 200° C., and is preferentially equal to 180° C. Reference may be made to patent EP 0 691 540 B1 with regard to the relevance of this temperature range for this type of rock sample.

According to one implementation of the invention according to which the sample analysed is a conventional source rock or an immature shale play (such as a black shale), the temperature T1 is between 280° and 320° C., and is preferentially equal to 300° C. Reference may be made to the document Behar et al., 2001 with regard to the relevance of this temperature range for this type of rock sample.

According to one implementation of the invention according to which the sample analysed is an oil-bearing shale play (such as an oil shale) or a gas-bearing shale play (such as a gas shale), the temperature T1 is between 80° and 120° C., and is preferentially equal to 100° C. Reference may be made to patent FR 3 021 748 (application US 2015/0346179) with regard to the relevance of this temperature range for this type of rock sample.

According to the invention, an amount of hydrocarbon-based compounds, an amount of carbon monoxide CO and an amount of carbon dioxide $CO_2$ released during the heating sequence in an inert atmosphere are measured. The measurements of hydrocarbon-based compounds can be carried out by a flame ionization detector or FID and the measurements of CO and of $CO_2$ can be carried out by an infrared IR spectrophotometer.

According to one preferred implementation of the invention, on the basis of the carbon monoxide and carbon dioxide measurements carried out during the heating sequence in an inert atmosphere, it is possible to determine:

An amount of carbon monoxide S3CO, of exclusively organic origin. This amount corresponds to the amount of carbon monoxide measured between the temperature T1 of the heating sequence in an inert atmosphere and a first intermediate temperature T1' of this heating sequence in an inert atmosphere, T1 being between 500 and 600° C., and preferentially equal to 550° C.;

An amount of carbon monoxide S3'CO, of both organic and mineral origin. This amount corresponds to the amount of carbon monoxide measured between the first intermediate temperature T1 of the heating sequence in an inert atmosphere, and the temperature T2 of the heating sequence in an inert atmosphere;

An amount of carbon dioxide $S3CO_2$, of exclusively organic origin, measured between the temperature T1 of the sequence in an inert atmosphere and a second intermediate temperature of the heating sequence in an inert atmosphere, of between 350° C. and 450° C., and preferentially equal to 400° C.

According to one implementation of the invention, a pyrolysis organic carbon content PC is determined according to a formula of the type:

$$PC(\text{wt \%}) = [Q*0.083] + \left[\left(S3CO + \frac{1}{2}S3'CO\right)*\frac{12}{280}\right] + \left[S3CO_2*\frac{12}{440}\right]$$

wherein Q is the amount of hydrocarbon-based compounds measured during the heating sequence in an inert atmosphere.

1.2. Oxidation of the Effluents from the Heating in an Inert Atmosphere

According to the invention, at least one portion of the effluents released during the pyrolysis is oxidized, this being as they are released. The sulfur-containing gases present in the pyrolysis effluents are thus oxidized to $SO_2$, as they are released. According to one implementation of the invention, this oxidation of the pyrolysis effluents is carried out by a combustion chamber, such as an oxidation furnace, in the presence of an oxygen-containing gas and optionally of a catalyst.

According to the invention, the $SO_2$ thus generated is continuously measured, as the pyrolysis is carried out, by an $SO_2$ detector such as an ultraviolet (UV) or infrared (IR) spectrophotometer. A measurement of the $SO_2$ released during the pyrolysis, as a function of the pyrolysis time and/or temperature, is thus obtained.

FIG. 1a presents an example of a curve (denoted C1) of measurement of the amount of $SO_2$ (more precisely the amplitude A measured by an $SO_2$ detector, such as an ultraviolet spectrophotometer) as a function of the pyrolysis time (denoted t), and also presents, as a dashed line, the evolution of the pyrolysis temperature (denoted T) as a function of the pyrolysis time. For this example and for illustrative purposes, the temperature T1 was chosen to be equal to 300° C., the temperature T2 was chosen to be equal to 650° C., the temperature T3 was chosen to be equal to 300° C. and the temperature T4 was chosen to be equal to 1200° C. It can be observed that this curve C1 comprises various peaks. In particular, the peak C which corresponds to the release during the pyrolysis of a portion of the sulfur contained in the pyrite, subsequently termed "pyrolysis pyritic sulfur" and denoted $S_{Pyrol}^{Pyrit}$, can be observed on this curve C1. Moreover, the first two peaks A and B of the curve C1 correspond to the sulfur contained in the heat-labile organic compounds, which are respectively vaporizable and thermally crackable.

According to the invention, the pyrolysis pyritic sulfur content $S_{Pyrol}^{Pyrat}$ is determined from the amount of $SO_2$ measured during this pyrolysis step. According to one implementation of the invention, the pyrolysis pyritic sulfur content $S_{Pyrol}^{Pyrit}$ can be determined from the area under the peak representative of the pyrolysis pyritic sulfur on the $SO_2$ measurement curve recorded during the pyrolysis phase (cf. peak C in FIG. 1a), divided by the weight of the sample analysed, weighted by a calibration coefficient for the pyrolysis sulfur. The pyrolysis pyritic sulfur content is expressed as weight percentage, that is to say by weight of pyrolysis pyritic sulfur, divided by the weight of the sample and multiplied by 100.

According to one implementation of the invention, the pyrolysis sulfur content $S_{Pyrol}$ of the sample analysed can be determined from the area under the curve of measurement of the $SO_2$ recorded during the pyrolysis-heating sequence, divided by the weight of the sample analysed, weighted by a calibration coefficient for the pyrolysis sulfur (respectively a calibration coefficient for the oxidation sulfur). These contents are expressed as weight percentage, that is to say by weight of pyrolysis sulfur, divided by the weight of the sample and multiplied by 100.

According to one implementation of the invention, a calibration coefficient for the pyrolysis sulfur can be determined from at least one reference sample, the sulfur content of which is known, which reference sample is subjected to a pyrolysis-heating sequence. The calibration coefficient for the pyrolysis sulfur is then determined from the area under the curve of measurement of the $SO_2$ released by this reference sample during a pyrolysis-heating sequence, itself divided by the weight of the reference sample. According to one implementation of the invention, the reference sample may be native sulfur for the determination of the calibration coefficient for the pyrolysis sulfur.

2. Heating Sequence in an Oxidizing Atmosphere (Oxidation)

According to the invention, the sample is heated under an oxidizing atmosphere between a temperature T3 of between 280° C. and 320° C., preferentially 300° C., and a temperature T4 of greater than or equal to 800° C. according to a predetermined temperature sequence.

According to one implementation of the invention, the temperature sequence for the heating in an oxidizing atmosphere may be a temperature gradient (or heating rate) of between 0.1° C./min and 30° C./min, preferentially between 20° C./min and 30° C./min, and very preferentially equal to 25° C./min. According to another implementation of the invention, the temperature sequence for the heating in an oxidizing atmosphere may comprise at least one stationary temperature phase (during which the temperature is kept constant) and at least one temperature gradient (or heating rate). It is possible for this gradient to be placed before or after the at least one stationary phase.

According to one implementation of the invention, this step can be carried out by an oxidation furnace with the pyrolysis residue being flushed with an air stream.

According to the invention, an amount of carbon monoxide is continuously measured during the heating sequence under an oxidizing atmosphere. The CO and $CO_2$ measurements performed during the oxidizing phase can be carried out by an infrared IR spectrophotometer.

According to the invention, a residual organic carbon content, subsequently denoted RC, is determined as a function of the CO and $CO_2$ measurements carried out during the heating, in an oxidizing atmosphere, of the residue from the pyrolysis.

According to one implementation of the invention, on the basis of the CO and $CO_2$ measurements carried out during the heating sequence in an oxidizing atmosphere, it is possible to determine at least:

An amount of carbon monoxide, subsequently denoted S4CO, which is exclusively of organic origin. This amount corresponds to the amount of carbon monoxide released between the temperature T3 of the heating sequence in an oxidizing atmosphere and an intermediate temperature of the heating sequence in an oxidizing atmosphere, of between 600° C. and 700° C., and preferentially equal to 650° C.;

An amount of carbon dioxide, subsequently denoted $S4CO_2$, which is exclusively of organic origin. This amount corresponds to the amount of carbon dioxide measured between the temperature T3 of the heating sequence in an oxidizing atmosphere and an intermediate temperature of the heating sequence in an oxidizing atmosphere, of between 600° C. and 700° C., and preferentially equal to 650° C.

According to this implementation of the invention, the residual organic carbon content RC is determined according to a formula of the type:

$$RC(\text{wt}\%) = \left[S4CO_2 * \frac{12}{440}\right] + \left[S4CO * \frac{12}{280}\right].$$

According to the invention, the following are also determined:

A hydrogen index, subsequently denoted HI, corresponds to the hydrogen content of the organic matter of the sample. According to the invention, this index is determined at least from the amount of hydrocarbon-based compounds measured during the heating sequence in an inert atmosphere and amounts of CO and $CO_2$ measured during the heating sequence in an inert atmosphere and during the heating sequence in an oxidizing atmosphere; and An oxygen index, subsequently denoted OI, which corresponds to the oxygen content of the organic matter of the sample. According to the invention, this index is determined at least from the amounts of CO and $CO_2$ measured during the heating sequence in an inert atmosphere and during the heating sequence in an oxidizing atmosphere.

According to one implementation of the invention, it is possible to determine:

the hydrogen index HI from a formula of the type:

$$HI = \frac{100 * S2}{TOC},$$

S2 corresponds to an amount of hydrogen-based compounds which were cracked during the heating of the sedimentary rock sample in an inert atmosphere, S2 being determined from the amount of hydrocarbon-based compounds Q released during the heating in an inert atmosphere, and TOC corresponds to the total organic carbon content, and is defined for this implementation of the invention according to the following formula: TOC(wt %)=PC+RC.

According to this implementation of the invention, the amount S2 of hydrocarbon-based compounds which were cracked during the heating of the sedimentary rock sample in an inert atmosphere corresponds to the hydrocarbon-based compounds which are not present in free-form in the rock sample under consideration. The specialist is perfectly aware of how to determine the amount S2 of hydrocarbon-based compounds which were cracked during the heating of the sedimentary rock sample in an inert atmosphere, from the amount of hydrocarbon-based compounds Q released during the heating in an inert atmosphere, in particular from a pyrogram representing the evolution of the amount of hydrocarbon-based compounds Q released during the heating in an inert atmosphere. Indeed, such a pyrogram generally exhibits several peaks. The first peak, often denoted S1, corresponds to the hydrocarbon-based compounds present in free-form in the sample. The following other peak(s) corresponding to the amount of hydrocarbon-based compounds which were cracked during the heating of the sedimentary rock sample in an inert atmosphere. It is thus possible to determine the amount S2 from the surface area of the peak(s) of the pyrogram different from the peak S1;

The oxygen index OI is expressed by a formula of the type:

$$OI = \left[\frac{100 * S3CO_2}{TOC}\right]$$

wherein $S3CO_2$ is the amount of carbon dioxide of organic origin-measured during the heating sequence in an inert atmosphere, and TOC is the total organic carbon content as defined above.

3. Quantification of the Pyritic Sulfur

According to the invention, during this step, the pyritic sulfur content $S^{Pyrit}$ contained in the sedimentary rock sample under consideration is quantified from the pyrolysis pyritic sulfur $S_{Pyrol}^{Pyrit}$ and from a weighting function $p(\alpha, \beta, \gamma)$ according to the following formula (cf. below section "Determination of the expression of $S^{Pyrit}$ as a function of $S_{Pyrol}^{Pyrit}$" below):

$$S^{Pyrit} = (\alpha, \beta, \gamma) \cdot S_{Pyrol}^{Pyrit}$$

with, according to the invention, $$p(\alpha, \beta, \gamma) = \frac{\left(1 + \frac{\beta}{1-\beta} + \frac{\gamma}{1-\gamma}\right)}{\alpha},$$

$S^{Pyrit}$ Is expressed as weight percentage, that is to say by weight of pyritic sulfur divided by the weight of the sample and multiplied by 100, and:

The parameter $\alpha$ represents the proportion of the pyritic sulfur released during the pyrolysis phase relative to its total sulfur, and can be seen as a degree of thermal degradation of the pyrite. According to one implementation of the invention, the parameter $\alpha$ is between 0.40 and 0.46, and is preferentially equal to 0.43;

The parameter $\beta$ represents the impact of the mineral matrix on the proportion of the pyritic sulfur released during the pyrolysis phase. Indeed, the mineral matrix reduces the amount of sulfur of the pyrite released during the pyrolysis phase. According to one aspect of the invention, the parameter $\beta$ may be between 0.04 and 0.97, as a function of the type of rock from which the sample studied originates. According to one implementation of the invention in which the rock sample studied is of clay type, the parameter $\beta$ may be between 0.04 and 0.7, and is preferentially equal to 0.38. According to one implementation of the invention in which the rock sample studied is of marl type, the parameter $\beta$ may be between 0.7 and 0.9, and is preferentially equal to 0.78. According to one implementation of the invention in which the rock sample studied is of limestone type, the parameter $\beta$ may be between 0.85 and 0.97, and is preferentially equal to 0.90;

The parameter $\gamma$ represents the impact of the organic matrix on the proportion of the pyritic sulfur released during the pyrolysis phase, and is predetermined from a formula of the type:

$$\gamma = f(OI, HI)$$

wherein $f$ is a function of at least the oxygen index OI and of the hydrogen index HI, with these indices having been determined during step 2 of the process according to the invention.

According to one preferred implementation of the invention, the function $f$ is a linear combination of the oxygen index OI and of the hydrogen index HI. This linear combination can be expressed according to a formula of the type: $\gamma = a*OI + b*HI + c$, wherein a, b and c are predetermined constants. Indeed, analyses carried out on varied samples (cf. below, section "calibration of the constants a, b and c of the parameter $\gamma$") have made it possible to demonstrate the linear behavior of the effect of the organic matrix with respect to the hydrogen and oxygen indices.

Advantageously, the constant a is between 0.28 and 0.46, and is preferentially equal to 0.37, and/or the constant b is between −0.005 and −0.007, and is preferentially equal to −0.006, and/or the constant c is between 4.99 and 6.49, and is preferentially equal to 5.74. Indeed, analyses carried out on varied samples (cf. below, section "calibration of the constants a, b and c of the parameter $\gamma$") have made it possible to demonstrate the linear behavior of the effect of the organic matrix with respect to the hydrogen and oxygen indices. Advantageously, $\gamma$ can range between 0.34 (wt. %) and 74 (wt. %).

Device for Implementing the Process According to the Invention

According to one implementation of the invention, steps 1 and 2 described above can be carried out by the Rock-Eval® device (IFP Energies nouvelles, France), developed by the applicant, and described in particular in patent EP 2 342 557, corresponding to U.S. Pat. No. 8,796,035. Indeed, the Rock-Eval® device comprises at least:
- an oven for pyrolysis in a non-oxidizing atmosphere,
- means for oxidation of the sulfur-containing effluents from pyrolysis,
- means for continuous measurement of the amount of $SO_2$ contained in the effluents after oxidation, such as an ultraviolet (UV) or infrared (IR) spectrophotometer;
- means for transferring the pyrolysis residues into an oxidation furnace;
- a furnace for oxidation in an oxidizing atmosphere;
- means for continuous measurement of the amount of $SO_2$ contained in the portion after oxidation, such as an ultraviolet (UV) or infrared (IR) spectrophotometer,
- means for measuring the hydrocarbon-based compounds released during the pyrolysis, such as a flame ionization detector (FID); and
- means for measuring the carbon monoxide (CO) and the carbon dioxide ($CO_2$), such as an infrared (IR) spectrophotometer.

According to one alternative of implementation of the process according to the invention, the process may also be carried out by a system comprising a single pyrolysis oven, which can operate in a non-oxidizing atmosphere and in an oxidizing atmosphere, cooperating with means for measuring the amount of sulfur dioxide ($SO_2$), means for measuring the amount of hydrocarbon-based compounds, and also means for measuring the carbon monoxide (CO) and the carbon dioxide ($CO_2$).

Variant 1: Quantification of the Organic Sulfur

Described below is a first variant of the process according to the invention, aimed at determining, in addition to the amount of pyritic sulfur present in the sample under consideration, the amount of organic sulfur present in this same sample. To do this, during step 2 of oxidation of the pyrolysis residue described above, the $SO_2$ generated by the oxidation of the pyrolysis residue and contained in the oxidation effluents is additionally measured. This $SO_2$ measurement is for example carried out by f a UV or IR spectrophotometer. A measurement of the $SO_2$ released during the oxidation, for example as a function of the oxidation time and/or temperature, is thus obtained.

Figure 1B:
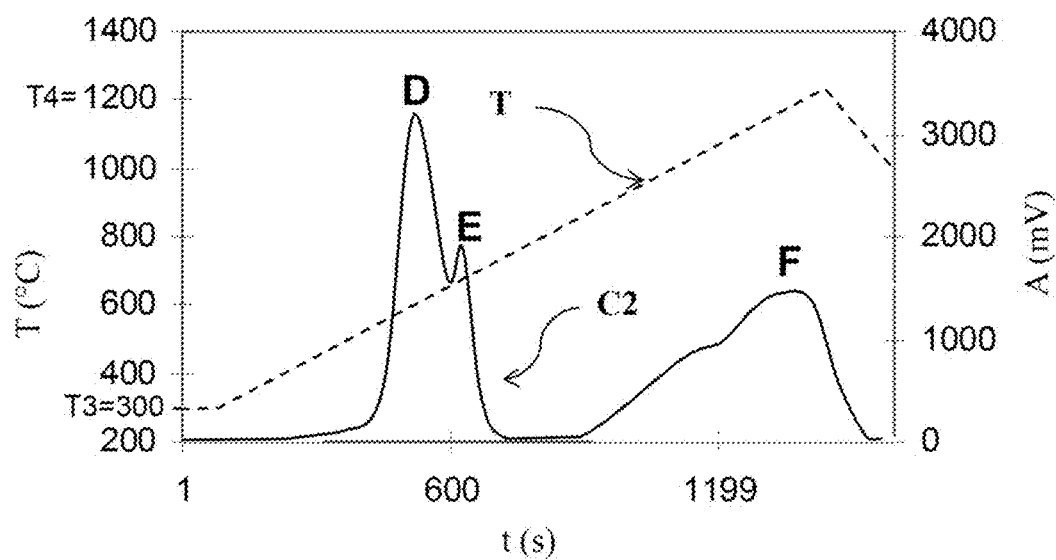
FIG. 1b presents an example of a measurement carried out by an $SO_2$ detector during a heating sequence in an oxidizing atmosphere to which a rock sample is subjected.

FIG. 1b presents an example of a curve (denoted C2) of measurement of the amount of $SO_2$ (more precisely the amplitude A measured by an $SO_2$ detector, such as an ultraviolet spectrophotometer) as a function of the oxidation time (denoted t), and also presents the evolution of the oxidation temperature (denoted T) as a function of the oxidation time. For this example and for illustrative purposes, the temperature T1 was chosen to be equal to 300° C., the temperature T2 was chosen to be equal to 650° C., the temperature T3 was chosen to be equal to 300° C. and the temperature T4 was chosen to be equal to 1200° C.

It can be observed that this curve C2 comprises various peaks. In particular, the peak F which corresponds to the release of the sulfur contained in the sulfates (subsequently termed "sulfate sulfur", and denoted $S_{Oxy}^{Sulfa}$) during the oxidation can be observed on the curve C2. Likewise, it can be observed that the curve C2 displays two first peaks D and E which are virtually combined, and which correspond respectively to organic sulfur contained in organic compounds, which are thermally refractory or else which were generated during the pyrolysis phase, and to pyritic sulfur. It is thus noted that the recording of the $SO_2$ released during the oxidation phase does not make it possible to distinguish between these two peaks and therefore between the organic sulfur and the pyritic sulfur.

According to this first variant of the invention, the content of pyrolysis sulfur $S_{Pyrol}$ released during the pyrolysis and the content of oxidation sulfur $S_{Oxy}$ released during the oxidation of the pyrolysis residue are quantified from, respectively, the $SO_2$ measurements carried out during the heating sequence in an inert atmosphere and during the heating sequence in an oxidizing atmosphere. According to this variant of the invention, the total sulfur content $S_{Total}$ is also determined as the sum of the two contents $S_{Pyrol}$ and $S_{Oxy}$. That is:

$$S_{Total} = S_{Pyrol} + S_{Oxy},$$

expressed as weight percentage (wt. %), that is by weight of total sulfur divided by the weight of the sample and multiplied by 100.

According to one implementation of this first variant of the invention, the pyrolysis sulfur content $S_{Pyrol}$ (respectively the oxidation the sulfur content $S_{Oxy}$) of the sample analysed can be determined from the area under the curve of measurement of the $SO_2$ recorded during the pyrolysis-heating sequence (respectively during the oxidizing heating sequence), divided by the weight of the sample analysed, weighted by a calibration coefficient for the pyrolysis sulfur (respectively a calibration coefficient for the oxidation sulfur). These contents are expressed as weight percentage, that is by weight of pyrolysis (respectively oxidation) sulfur, divided by the weight of the sample and multiplied by 100.

According to this first variant of the invention, the organic sulfur content $S^{Org}$ contained in the rock sample under consideration can be determined from at least the difference between the total sulfur content $S_{Total}$ and the pyritic sulfur content $S^{Pyrit}$.

According to a first implementation of this first variant of the invention according to which the temperature at the end of oxidation T4 is between 800° C. and 900° C., the organic sulfur content $S^{Org}$ contained in the sample can be determined according to a formula of the type:

$$S^{Org} = S_{Total} - S^{Pyrit}$$

According to a second implementation of this first variant of the invention according to which the temperature at the end of oxidation T4 is between 1150° C. and 1250° C., preferentially 1200° C., the organic sulfur content $S^{Org}$ contained in the sample can be determined in the following way:
- a sulfate sulfur content $S_{Oxy}^{Sulfa}$ is quantified from the area under the peak representative of the sulfate sulfur of the curve of measurement of the $SO_2$ recorded during the oxidation phase, divided by the weight of the sample analysed, and weighted by a calibration coefficient for the oxidation sulfur (cf. step 3 above for the determination of this calibration coefficient);
- the organic sulfur content $S^{Org}$ is determined according to a formula of the type:

$$S^{Org} = S_{Total} - S^{Pyrit} - S_{Oxy}^{Sulfa}.$$

Indeed, for this implementation variant, it is possible to distinguish the peak $S_{Oxy}^{Sulfa}$ (cf. peak F in FIG. 1a) which corresponds to the release during the oxidation of the sulfur contained in the sulfates, occurring for the high temperatures. The determination of the organic sulfur content is more precise according to this second implementation of the invention.

Variant 2: Calibration of the Parameters α, β and γ

According to one implementation of the invention, the parameters α and/or β and/or γ as defined above can be calibrated prior to the implementation of the process according to the invention or else during the implementation of the process according to the invention, for example prior to step 1, to step 2 or to step 3 described above, or else in parallel with steps 1 and/or 2.

Calibration of the Parameter α

According to one implementation of the invention, the parameter α can be calibrated by estimating the proportion of the pyritic sulfur released during the pyrolysis phase relative to the total sulfur from at least one sample of pure igneous pyrite. According to one implementation of the invention, a "pure" pyrite can be obtained by cleaning a natural pyrite to remove its impurities by means of chemical attacks.

An example of calibration of the parameter α is described below. Four samples derived from a single sample of pure igneous pyrite (denoted, respectively, E1, E2, E3, E4), having different weights (respectively 2 mg, 3 mg, 4 mg and 8 mg) are each subjected to a pyrolysis by f the Rock-Eval® device (IFP Energies nouvelles, France). In particular, for this example of calibration of the parameter a, each sample was placed in the pyrolysis oven of the Rock-Eval® device, then the sample was heated between 300° C. and 650° C., with a temperature gradient of 25° C./min and under a nitrogen stream at 150 ml/min. The sulfur-containing effluents released by each sample of pure igneous pyrite under consideration were then entrained by the nitrogen stream to the combustion chamber (oxidation furnace) of the Rock-Eval® device, where they were converted into $SO_2$ in a continuous stream, then the $SO_2$ was entrained to an $SO_2$ detector where it was continuously quantified by the $SO_2$ detector of the Rock-Eval® device. The solid residue of each sample of igneous pyrite, obtained at the outcome of the pyrolysis sequence, was then placed in the oxidation furnace of the Rock-Eval® device, then the sample was heated between 300° C. and 850° C., with a temperature gradient of 20° C./min and under an air stream at 100 ml/min. The $SO_2$ effluents released were entrained to an $SO_2$ detector where they were continuously quantified by the $SO_2$ detector of the Rock-Eval® device.

Figure 2:
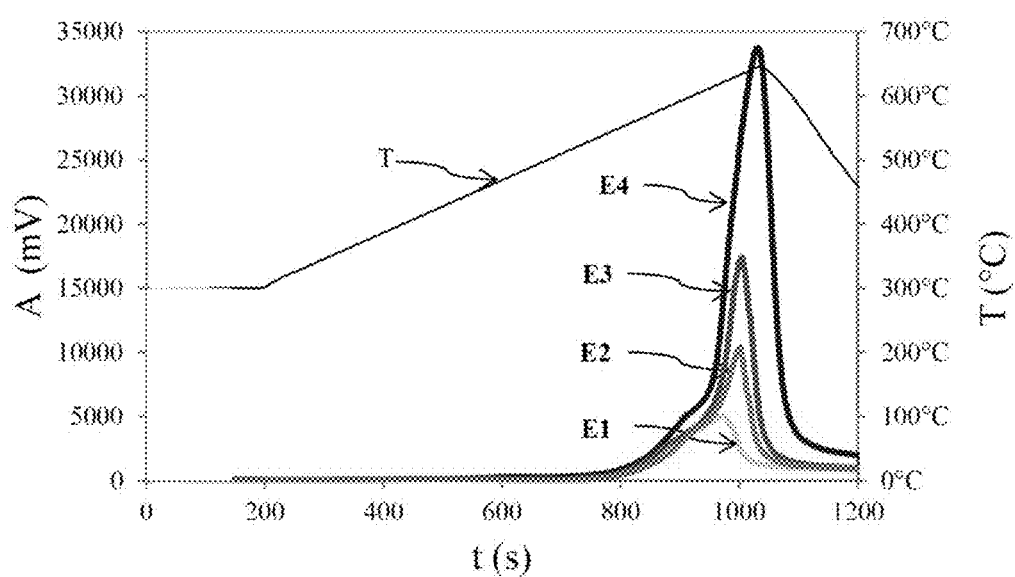
FIG. 2 presents representative curves of the amount of $SO_2$ released by four samples of pure igneous pyrite of distinct weights, during a heating sequence under an inert atmosphere.

FIG. 2 presents the recording in the time t of the amount of $SO_2$ (more precisely the magnitude) released by the samples E1, E2, E3 and E4 during the pyrolysis phase as described above. The curve T also presented in this FIG. 2 corresponds to the evolution of the temperature to which each of the samples under consideration is subjected during this same pyrolysis phase. It is thus possible in particular to observe, in this figure, the presence of the peaks representative of the thermal degradation of the pyrite at the various weights analysed during the pyrolysis phase. The pyrolysis sulfur content of the sample of igneous pyrite (pyrolysis pyritic sulfur content) was calculated by multiplying, by the sulfur content of the reference sample, the area under each of the curves E1, E2, E3 and E4, divided by the weight of the sample, and related back to the area under the curve of measurement of the $SO_2$ released by a reference sample (such as native sulfur) during the pyrolysis-heating sequence, itself divided by the weight of the reference sample. The ratio between this pyrolysis pyritic sulfur content and the total sulfur content of the pyrite is calculated. The results show that, whatever the weight analysed, the weight proportion of the pyritic sulfur that is released during the pyrolysis is 0.43±0.03 wt %. The remaining proportion of pyritic sulfur at the outcome of the pyrolysis (0.57±0.03 wt %) is then released during the oxidation phase.

Thus, the calibration as described above makes it possible to determine that the parameter α is between 0.40 and 0.46, and is equal to 0.43 on average.

Calibration of the Parameter β

According to one implementation of the invention, the parameter β which represents the impact of the mineral matrix on the amount of the sulfur of the pyrite released during the pyrolysis phase can be calibrated from at least one mixture of pyrite and of at least one type of mineral This mixture is representative of the rock sample to be studied by the process according to the invention.

An example of calibration of the parameter β for various types of minerals is described below. For this example of calibration of the parameter B, mixtures were prepared from the two major groups of minerals below:

clayey/silicate-based minerals, such as
    Silica (Fontainebleau sand, France) the mixture prepared with silica is the reference mixture since silica is known to be non-reactive;
    Kaolinite (Reference: CMS KGa 1b);
    Smectite (Reference: Mx80);
    Illite (Velay clay, France): since this sample naturally contains carbonates, it was decarbonated with hydrochloric acid;
carbonate-based minerals, such as:
    Calcite (France);
    Dolomite (Euguy, Spain);
    Siderite (Peru).

The following mixtures are then prepared:
2 mg of pyrite+98 mg of each clayey/silicate-based mineral;
2 mg of pyrite+58 mg of each carbonate-based mineral;
2 mg of pyrite+98 mg of clays (all the clayey/silicate-based minerals in equal parts ¼; ¼; ¼; ¼);
2 mg of pyrite+58 mg of carbonates (all the carbonate-based minerals in equal parts ⅓; ⅓; ⅓);
2 mg of pyrite+58 mg of clays and of carbonates in various proportions, that is to say
    93% of clays and 7% of carbonates;
    69% of clays and 31% of carbonates;
    51% of clays and 49% of carbonates;
    26% of clays and 74% of carbonates.

These various samples are then subjected to steps 1 and 2 as described above by use of the Rock-Eval® device (IFP Energies nouvelles, France). More specifically, each sample is placed in the pyrolysis oven of the Rock-Eval® device, then the sample is heated between 300° C. and 650° C., with a temperature gradient of 25° C./min and under a nitrogen stream at 150 ml/min. According to one implementation of the invention, the sulfur-containing effluents released by each sample are entrained by a nitrogen stream to the combustion chamber (oxidation furnace) of the Rock-Eval® device where they are converted into $SO_2$ in a continuous stream, then the $SO_2$ is entrained to the $SO_2$ detector of the Rock-Eval® device where it is continuously quantified. The solid residue of each sample obtained at the outcome of the pyrolysis sequence is then placed in the oxidation furnace of the Rock-Eval® device, then the sample is heated between 300° C. and 850° C., with a temperature gradient of 20° C./min and under an air stream at 100 ml/min. The $SO_2$ effluents released are entrained to an $SO_2$ detector where they are continuously quantified by the $SO_2$ detector of the Rock-Eval® device.

The term "effect of the mineral matrix" is subsequently given to the magnitude which is expressed according to a formula of the type:

$$E_{Min} = \frac{S_{Pyrol}^{Pyrit,ref} - S_{pyrol}^{Pyrit,Matrix}}{S_{Pyrol}^{Pyrit,ref}} \times 100,$$

wherein $S_{Pyrol}^{Pyrit,ref}$ is the pyrolysis pyritic sulfur released by a reference sample (consisting of pure igneous pyrite and of silica) and $S_{pyrol}^{Pyrrit,Matrix}$ is the pyrolysis pyritic sulfur released by a mixture under consideration (pure igneous pyrite plus a mineral or a mixture of minerals). In order to evaluate this magnitude, the pyrolysis pyritic sulfur content is determined, for a reference sample $S_{Pyrol}^{Pyrit,ref}$ and for a mixture under consideration $S_{Pyrol}^{Pyrit,Matrix}$.

Figure 3A:
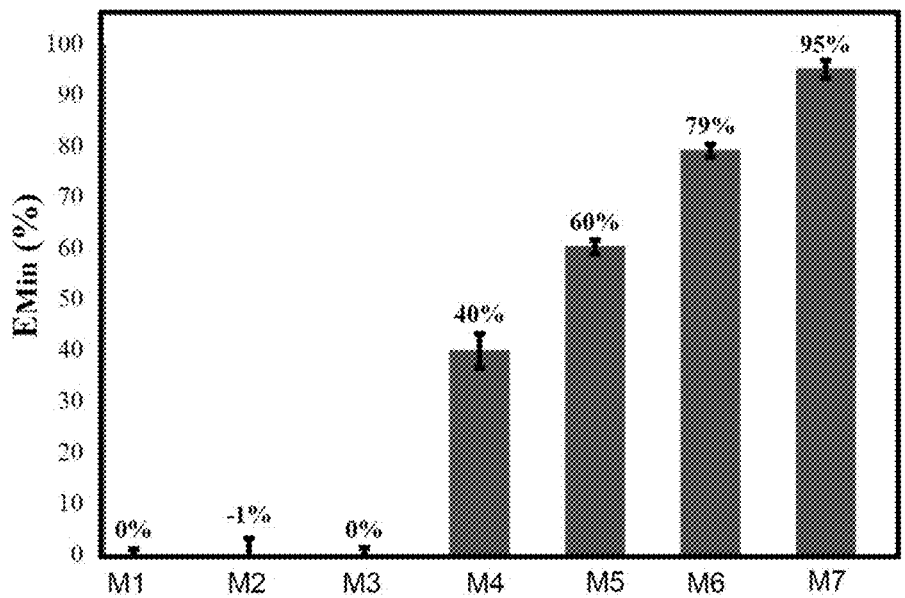
FIG. 3a presents a representative histogram of the effect of the mineral matrix as a function of the class of mineral mixtures under consideration.

FIG. 3a presents a representative histogram of the effect $E_{Min}$ of the mineral matrix as a function of the class of mixtures under consideration in the case of clayey/silicate-based and carbonate-based minerals, more specifically for the following classes of mixtures:

M1: mixtures consisting of pyrite and of quartz (reference sample);
M2: mixtures consisting of pyrite and of kaolinite;
M3: mixtures consisting of pyrite and of illite;
M4: mixtures consisting of pyrite and of smectite;
M5: mixtures consisting of pyrite and of calcite;
M6: mixtures consisting of pyrite and of dolomite;
M7: mixtures consisting of pyrite and of siderite.

Figure 3B:
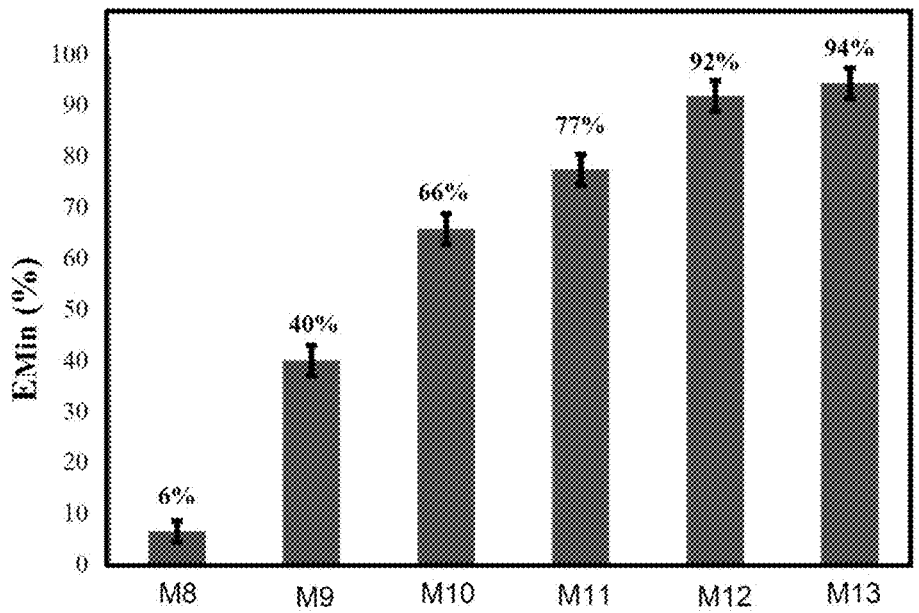
FIG. 3b presents a representative histogram of the mean effect of clays, of carbonates and of intermediate formations on the proportion of sulfur of the pyrite released during the pyrolysis, as a function of the class of mineral mixtures under consideration.

FIG. 3b presents a representative histogram of the mean effect $E_{Min}$ of clays, of carbonates and of intermediate formations on the proportion of sulfur of the pyrite released during the pyrolysis, for the following mixtures:

M8: mixtures consisting of 100% of clays;
M9: mixtures consisting of 93% of clays and of 7% of carbonates;
M10: mixtures consisting of 69% of clays and of 31% of carbonates;
M11: mixtures consisting of 51% of clays and of 49% of carbonates;
M12: mixtures consisting of 26% of clays and of 74% of carbonates;
M13: mixtures consisting of 100% of carbonates.

FIGS. 3a and 3b also exhibit the error bars for each histogram bar.

These error bars were obtained by estimating a standard deviation established from a repetition of the analyses as described above.

Thus, the results obtained by carrying out the method for calibration of the parameter β as described above for the various mixtures described above demonstrate the fact that the mineral matrix can reduce the proportion of sulfur of the pyrite released during the pyrolysis phase. However, this effect is very variable according to the type of mineral present. The relative reduction of the proportion of sulfur released by the pyrite in pyrolysis ranges between 0% and 40% in the presence of clayey/silicate-based minerals and between 60% and 98% in the presence of carbonate-based minerals (cf. FIG. 3a). The mean effect of the clays comes to 6%, whereas that of the carbonates reaches 93% (cf. FIG. 3b). Between these two poles, an increasing evolution of the effect of the mineral matrix $E_M$ as a function of the proportion of clays and carbonates in the mixture is observed (cf. FIG. 3b).

Figure 3C:
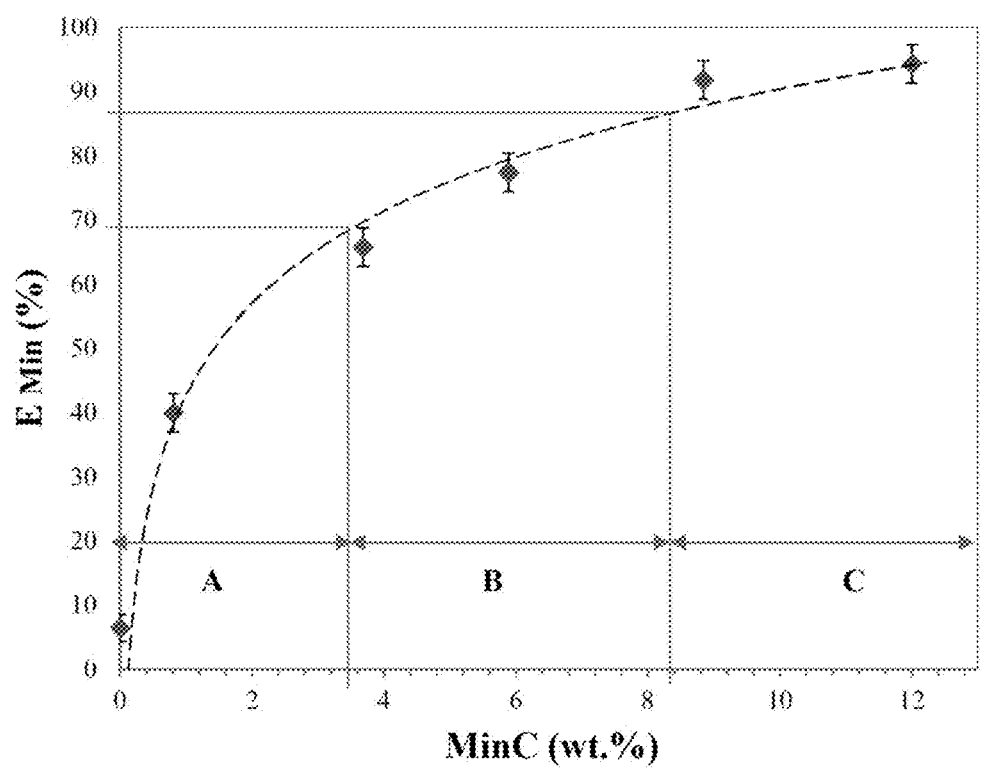
FIG. 3c presents the evolution of the effect of the mineral matrix, as a function of the mineral carbon.

FIG. 3c shows the evolution of the effect $E_{Min}$ of the mineral matrix as a function of the mineral carbon (hereinafter denoted MinC), which is a parameter that can be measured for example with the Rock-Eval® device (IFP Energies nouvelles, France), and which is an indicator of the carbonate content of the mixtures. It can be observed in this figure that the MinC varies over a range of between 0 wt % and 12 wt %, which corresponds to a calcite equivalent between 0 wt % and 100 wt %. By virtue of this parameter, three lithology types can be defined: clays, marls and limestones. The region (A) of FIG. 3c represents the region of the clays, which have carbonate-calcite equivalent contents of between 0 wt % and 30 wt % (0≤MinC clays<3.6 wt %). In this region of the clayey formations, the effect of the matrix on the amount of sulfur of the pyrite released during the pyrolysis phase ranges between 6% and 70%, with a mean of 38%. The region (B) of FIG. 3c represents the region of the marls, which have carbonate-calcite equivalent contents of between 30% and 70% (3.6≤MinC marls<8.4 wt %). In this region of the marl formations, the mean effect value of the matrix on the amount of sulfur of the pyrite released during the pyrolysis phase ranges between 70% and 87%, with a mean of 78%. The region (C) of FIG. 3c represents the region of the limestones, which have carbonate-calcite equivalent contents of between 70% and 100% (8.4 wt %≤MinC limestones≤12 wt %). In this region of the limestone formations, the mean effect value of the matrix on the amount of sulfur of the pyrite released during the pyrolysis phase ranges between 87% and 94%, with a mean of 90%.

Thus, the parameter β ranges between 0.06 and 0.94 depending on the type of sedimentary formation, and more specifically, in the case of:

Clays: the parameter β is on average equal to 0.38;
Marls: the parameter β is on average equal to 0.78;
Limestones: the parameter β is on average equal to 0.90.

Calibration of the Constants a, b and c of the Parameter γ

This step can be carried out in the context of the preferred implementation of the process according to the invention, according to which the parameter γ is written in the form:

$$\gamma = a*OI + b*HI + c,$$

wherein a, b and c are predetermined constants.

According to one implementation of the invention comprising a step of calibration of the constants a, b and c of the parameter γ, it is possible to prepare mixtures consisting of pyrite and of various types of organic matter conventionally denoted:

Type I: lacustrine organic matter, such as the "green river shales" (Eocene, USA);
Type II: marine organic matter, such as the "paper shales" of the Paris Basin (Toarcian, France);
Type II: marine organic matter originating from the ODP 959 wells (Coniacian-Santonian, Ivory Coast-Ghana);
Type II oxidized: marine organic matter, such as the "paper shales" of the Paris Basin (Toarcian, France), artificially oxidized according to the method described in the document Landais et al., 1991;
Type IIS: marine organic matter rich in organic sulfur, such as the "Phosphoria Formation" (Permian, USA);
Type III: terrestrial organic matter, such as the "Calvert Bluff Formation" (Paleocene, USA);

Type III oxidized: terrestrial organic matter, such as the "Calvert Bluff Formation" (paleocene, USA), artificially oxidized according to the method described in the document Landais et al., 1991;

mixtures of types II and III: mixtures of marine organic matter, such as the "paper shales" of the Paris Basin (Toarcian, France) and of terrestrial organic matter, such as the "Calvert Bluff Formation" (Paleocene, USA).

The term "effect of the organic matrix" is subsequently given to the magnitude which is expressed according to the following formula:

$$E_{Org} = \frac{S_{Pyrol}^{Pyrit+MOobtained} - S_{pyrol}^{Pyrit+MOexpected}}{S_{Pyrol}^{Pyrit+MOexpected}} \times 100,$$

wherein $S_{Pyrol}^{Pyrit+MO\ obtained}$ is the pyrolysis pyritic sulfur obtained after the analysis of the mixture formed of pyrite and of organic matter (as described in step 1 above), and $S_{Pyrol}^{Pyrit+MO\ expected}$ is the expected value of pyrolysis pyritic sulfur of the mixture. This theoretical reference value is calculated as follows:

each sample of organic matter alone is analysed, by means of the Rock-Eval® device (IFP Energies nouvelles, France), in order to quantify its pyrolysis pyritic sulfur content (as described in step 1 above);

the pyrite alone is analysed, by the Rock-Eval® device (IFP Energies nouvelles, France), in order to quantify its pyrolysis pyritic sulfur content (as described in step 1 above);

the pyritic sulfur from the pyrolysis of the pyrite and the pyritic sulfur from the pyrolysis of the organic matter are added proportionally, as a function of the pyrite/organic matter ratio.

Moreover, the hydrogen index HI and the oxygen index OI are determined for each of the samples described above, as described in step 2 above, by the Rock-Eval® device (IFP Energies nouvelles, France). In particular, to do this, the pyrolysis organic carbon content PC is determined according to the formula:

$$PC(\text{wt \%}) = [Q*0.083] + \left[S3CO * \frac{12}{280}\right] + \left[S3CO_2 * \frac{12}{440}\right]$$

the residual organic carbon content RC is determined according to the formula:

$$RC(\text{wt \%}) = \left[S4CO_2 * \frac{12}{440}\right] + \left[S4CO * \frac{12}{280}\right]$$

the oxygen index OI is determined according to the formula: OI=

$$\left[\frac{\left(S3CO * \frac{16}{28}\right) + \left(S3CO_2 * \frac{32}{44}\right)}{RC + PC}\right]$$

the hydrogen index HI is determined according to the formula:

$$HI = \frac{100*S2}{RC+PC}$$

Then, a multivariable regression relating to the effect of the organic matrix $E_{Org}$ is performed as a function of the oxygen index OI and of the hydrogen index HI and the constants a, b, and c of the parameter γ as defined above and which is expressed in the form: γ=a*OI+b*HI+c are determined. The linear regression thus described makes it possible to obtain the following formula for the parameter γ representing the effect of the organic matrix:

γ=0.37*OI−0.006*HI+5.74

Figure 4:
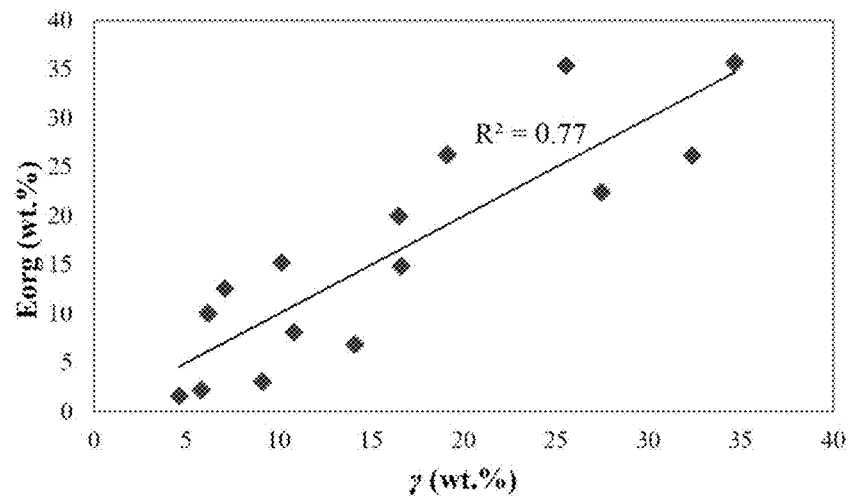
FIG. 4 presents a comparison between the organic effect obtained by use of analyses of mixtures of pyrite and of various types of organic matter and the organic effect determined by means of the process according to the invention.

FIG. 4 presents the comparison between the value of γ thus determined by regression (continuous straight-line) and the values determined by measurements on the various samples (diamonds) as described above. A good correlation between the values taken by γ and the values of $E_{Org}$ determined by measurements (the linear regression coefficient R2 is 0.77) can be observed, which demonstrates that it is possible to reliably predict the effect of the organic matter from the oxygen index OI and the hydrogen index HI. Moreover, on the basis of these experiments carried out on various types of sample, the following error bars are defined on each of the constants:

a=0.37±0.09 b=−0.006±0.001 c=5.74±0.75

Moreover, in the knowledge that generally 0≤HI(mg HC/g TOC)≤900 and 0≤OI(mg CO₂/g TOC)≤200, γ can range between 0.34 wt. % (HI=900; OI=0) and 74 wt. % (HI=0; OI=200).

Determination of the Expression of the Weighting Function

The weighting function p(α,β,γ) of the process according to the invention is different from that of patent application FR 17/59447 (filing number). The justification of the expression of the weighting function of the process according to the invention is detailed below.

$S_{pyrol}^{Pyrit}$ represents a pyrolysis pyritic sulfur content which was reduced by the presence of the mineral matrix and of the organic matrix. It is thus advisable, in a first step, to correct the pyrolysis pyritic sulfur content $S_{pyrol}^{Pyrit}$ of the mineral effect and of the organic effect. This then makes it possible to quantify the total pyrolysis pyritic sulfur $S_{pyrol\ total}^{Pyrit}$, and then to deduce the total pyritic sulfur $S^{Pyrit}$.

Correction of the Mineral Effect Corrβ:

The mineral effect β represents the proportion of the pyrolysis pyritic sulfur that is retained in the mineral matrix. Thus, knowing the effect of the mineral matrix β, it is possible to find the pyrolysis pyritic sulfur without this effect of the mineral matrix $S_{Pyrol}^{Pyrit\ without\ Emin}$. The formula of the mineral effect can be written in the following way:

$$\beta = \frac{S_{Pyrol}^{Pyrit without Emin} - S_{pyrol}^{Pyrit}}{S_{Pyrol}^{Pyrit without Emin}}$$

$$\beta = 1 - \frac{S_{pyrol}^{Pyrit}}{S_{Pyrol}^{Pyrit without Emin}}$$

-continued $$\frac{S^{Pyrit}_{pyrol}}{S^{Pyritwithout\,Emin}_{Pyrol}} = 1 - \beta$$

$$S^{Pyritwithout\,Emin}_{Pyrol} = \frac{S^{Pyrit}_{pyrol}}{1-\beta}$$

Corrβ, which represents the amount of the pyrolysis pyritic sulfur that was retained in the mineral matrix, is then defined according to the following formula:

$$Corr\beta = S^{Pyritwithout\,Emin}_{Pyrol} - S^{Pyrit}_{pyrol}$$

$$Corr\beta = \frac{S^{Pyrit}_{pyrol}}{1-\beta} - S^{Pyrit}_{pyrol}$$

$$Corr\beta = S^{Pyrit}_{pyrol}\left(\frac{1}{1-\beta} - 1\right)$$

$$Corr\beta = S^{Pyrit}_{pyrol}\left(\frac{\beta}{1-\beta}\right)$$

Correction of the organic effect $CorrE_{Org}$:

The organic effect γ represents the proportion of the pyrolysis pyritic sulfur that is retained in the organic matrix. Thus, knowing the effect of the organic matrix γ, it is possible to find the pyrolysis pyritic sulfur without this effect of the organic matrix $S_{Pyrol}^{Pyrit\,without\,Eorg}$. The formula of the organic effect can be written in the following way:

$$\gamma = \frac{S^{Pyritwithout\,Eorg}_{Pyrol} - S^{Pyrit}_{pyrol}}{S^{Pyritwithout\,Eorg}_{Pyrol}}$$

$$\gamma = 1 - \frac{S^{Pyrit}_{pyrol}}{S^{Pyritwithout\,Eorg}_{Pyrol}}$$

$$\frac{S^{Pyrit}_{pyrol}}{S^{Pyritwithout\,Eorg}_{Pyrol}} = 1 - \gamma$$

$$S^{Pyritwithout\,Eorg}_{Pyrol} = \frac{S^{Pyrit}_{pyrol}}{1-\gamma}$$

$CorrE_{org}$, which represents the amount of the pyrolysis pyritic sulfur that was retained in the organic matrix, is then defined according to the following formula:

$$Corr\gamma = S^{Pyritwithout\,Eorg}_{Pyrol} - S^{Pyrit}_{pyrol}$$

$$Corr\gamma = \frac{S^{Pyrit}_{pyrol}}{1-\gamma} - S^{Pyrit}_{pyrol}$$

$$Corr\gamma = S^{Pyrit}_{pyrol}\left(\frac{1}{1-\gamma} - 1\right)$$

$$Corr\gamma = S^{Pyrit}_{pyrol}\left(\frac{\gamma}{1-\gamma}\right)$$

Calculation of the Total Pyrolysis Pyritic Sulfur $S^{Pyrit}_{pyrol\,total}$

The total pyrolysis pyritic sulfur $S^{Pyrit}_{pyrol\,total}$ is then obtained from the sum of $S^{Pyrit}_{pyrol}$ (the pyrolysis sulfur content reduced by the presence of the mineral matrix and of the organic matrix), Corrβ (the amount of the pyrolysis pyritic sulfur that was retained in the mineral matrix) and Corrγ (the amount of the pyrolysis pyritic sulfur that was retained in the organic matrix) in the following way:

$$S^{Pyrit}_{pyrol\,total} = S^{Pyrit}_{pyrol} + Corr\beta + Corr\gamma$$

$$S^{Pyrit}_{pyrol\,total} = S^{Pyrit}_{pyrol} + S^{Pyrit}_{pyrol}\left(\frac{\beta}{1-\beta}\right) + S^{Pyrit}_{pyrol}\left(\frac{\gamma}{1-\gamma}\right)$$

$$S^{Pyrit}_{pyrol\,total} = S^{Pyrit}_{pyrol}\left(1 + \frac{\beta}{1-\beta} + \frac{\gamma}{1-\gamma}\right)$$

Calculation of the Total Pyritic Sulfur $S^{Pyrit}$

The total pyritic sulfur $S^{Pyrit}$ is calculated from the total pyrolysis pyritic sulfur $S^{Pyrit}_{pyrol\,total}$ and from the parameter α (the proportion of the total pyrolysis pyritic sulfur $S^{Pyrit}_{pyrol\,total}$ relative to the total pyritic sulfur $S^{Pyrit}$):

$$S^{Pyrit} = \frac{S^{Pyrit}_{pyrol\,total}}{\alpha}$$

$$S^{Pyrit} = S^{Pyrit}_{pyrol} * \frac{\left(1 + \frac{\beta}{1-\beta} + \frac{\gamma}{1-\gamma}\right)}{\alpha}$$

$$S^{Pyrit} = p(\alpha, \beta, \gamma) * S^{Pyrit}_{pyrol}$$

The following expression for the weighting function makes possible to determination of the total pyritic sulfur $S^{Pyrit}$ from the pyrolysis pyritic sulfur $S^{Pyrit}_{pyrol}$ measured is thus deduced therefrom:

$$p(\alpha, \beta, \gamma) = \frac{\left(1 + \frac{\beta}{1-\beta} + \frac{\gamma}{1-\gamma}\right)}{\alpha}$$

APPLICATION EXAMPLES

The application example below aims to evaluate the quality of the results obtained by carrying out the process according to the invention. To do this, various mixtures are produced, formed from nine samples of sedimentary rocks containing only organic sulfur, this being in a known amount, to which known weights of pyrite are added. The rock samples originate from three different formations ("Orbagnous", "Phosphoria" and "Limagne") and were taken from various levels of these formations. The characteristics of these nine samples of sedimentary rocks are summarized in the first nine rows of Tables 1a and 1b below. Different weights of pyrite were added to these nine samples, according to the characteristics summarized in rows 10 and 11 of Tables 1a and 1b below. In this way, 14 mixtures of "pyrite+Orbagnous" type (type subsequently denoted EXA), 6 mixtures of "pyrite+Phosphoria" type (type subsequently denoted EXB), and 8 mixtures of "pyrite+Limagne" type (type subsequently denoted EXC) are produced.

The pyritic sulfur and organic sulfur contents of each of these mixtures are then determined, on the one hand, by the process according to the invention and, on the other hand, by the process according to the prior art described in patent application FR 17/59447.

The process according to the invention is carried out by the Rock-Eval® device (IFP Energies nouvelles, France).

More specifically, each mixture is placed in the pyrolysis oven of the Rock-Eval® device, then the mixture is heated between 300° C. and 650° C., with a temperature gradient of 25° C./min and under a nitrogen stream at 150 ml/min. According to one implementation of the invention, the sulfur-containing effluents released by each sample are entrained by a nitrogen stream to a combustion chamber (also referred to as oxidation furnace) of the Rock-Eval® device where they are converted into $SO_2$ in a continuous stream, then the $SO_2$ is entrained to the $SO_2$ detector of the Rock-Eval® device where it is continuously quantified. At the outcome of the pyrolysis, each residue of the mixture is transferred from the pyrolysis oven to the oxidation furnace of the Rock-Eval® device, then the sample is heated between 300° C. and 850° C. or 1200° C. depending on the implementation, with a temperature gradient of 20° C./min and under an air stream at 100 ml/min. The $SO_2$ effluents released by this oxidation are entrained to the $SO_2$ detector of the Rock-Eval® device where they are continuously quantified. The total sulfur, pyritic sulfur and organic sulfur contents of each mixture are determined by carrying out the process according to the invention as described above.

Figure 5A:
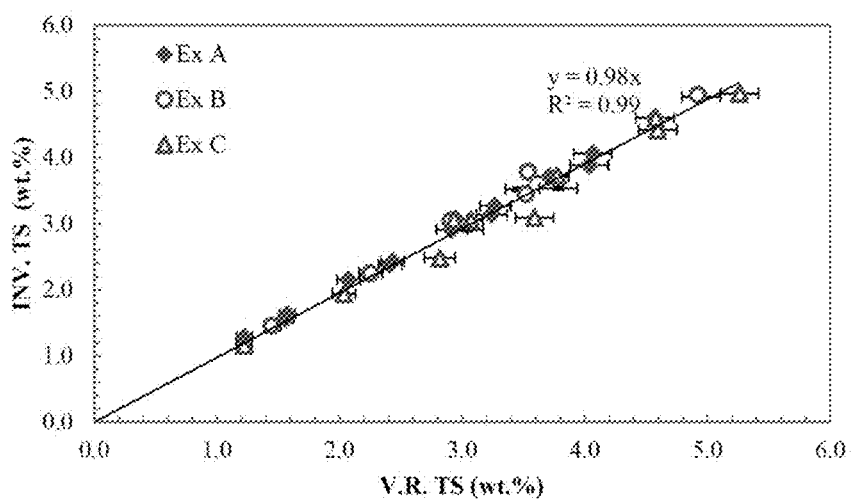
FIG. 5a presents the total sulfur content determined by use of the process according to the invention for samples of various type, as a function of the actual total sulfur content of these samples.
Figure 5B:
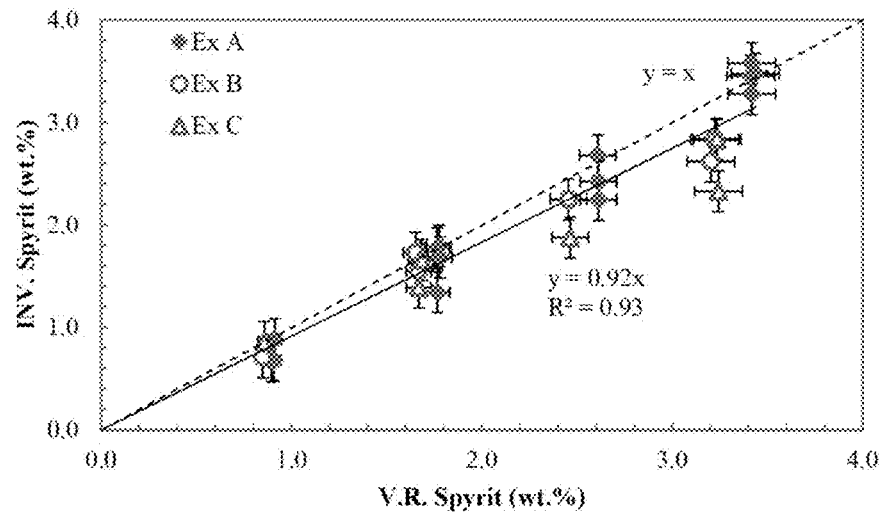
FIG. 5b presents the pyritic sulfur content determined by use of the process according to the invention for samples of various type, as a function of the actual pyritic sulfur content of these samples.
Figure 5C:
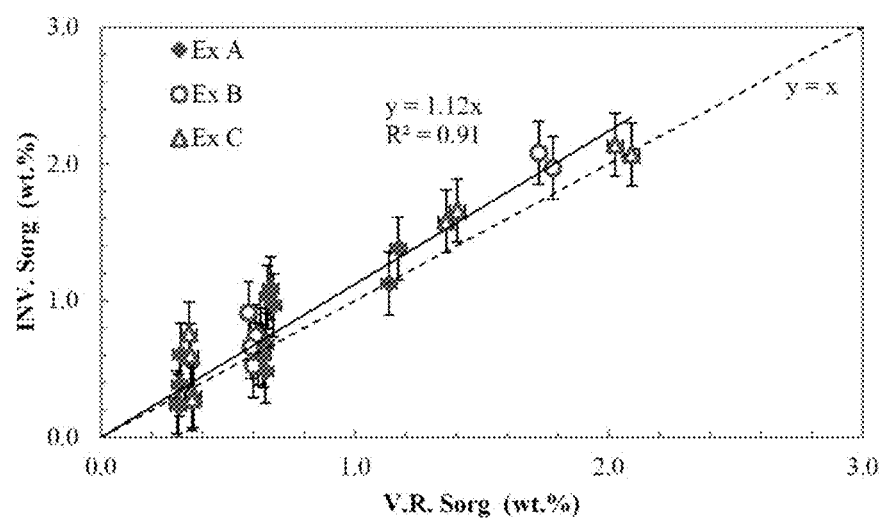
FIG. 5c presents the organic sulfur content determined by use of the process according to the invention for samples of various type, as a function of the actual organic sulfur content of these samples.

FIGS. 5a, 5b and 5c present respectively the evolution of the total sulfur (INV TS), pyritic sulfur (INV $S_{pyrit}$) and organic sulfur (INV $S_{org}$) contents obtained by means of the process according to the invention, as a function of the reference contents, respectively, of total sulfur (VR TS), of pyritic sulfur (VR $S_{pyrit}$) and of organic sulfur (VR $S_{org}$) for each of the mixtures of the EXA type (that is to say 14 "pyrite+Orbagnous" mixtures), for each of the mixtures of the EXB type (that is to say 6 "pyrite+Phosphoria" mixtures) and for each of the mixtures of the EXC type (that is to say 8 "pyrite+Limagne" mixtures).

A very good correlation between the total sulfur, pyritic sulfur and organic sulfur contents determined using the process according to the invention and the reference contents of total sulfur, of pyritic sulfur and of organic sulfur can be observed in FIGS. 5a, 5b and 5c (correlation with a slope close to 1). This confirms the precision of the determination of the pyritic sulfur content and the organic sulfur content of a sample by means of the process according to the invention.

Figure 5D:
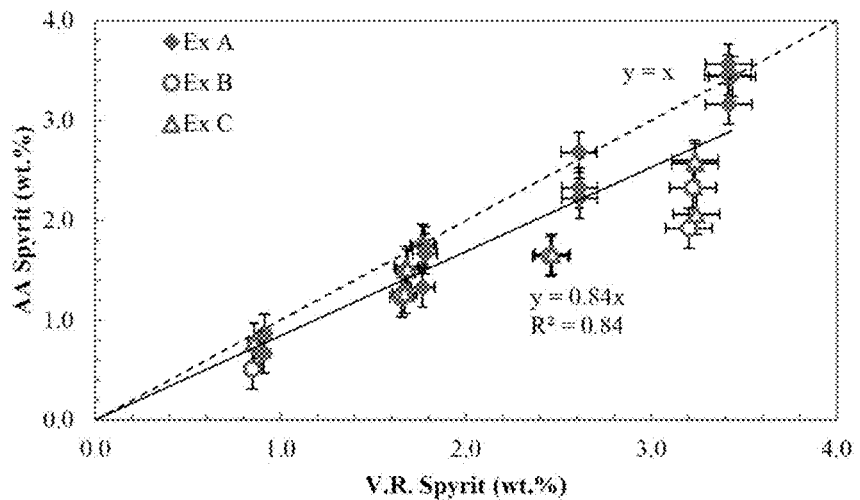
FIG. 5d presents the pyritic sulfur content determined by use of a process according to the prior art for samples of various type, as a function of the actual pyritic sulfur content of these samples.
Figure 5E:
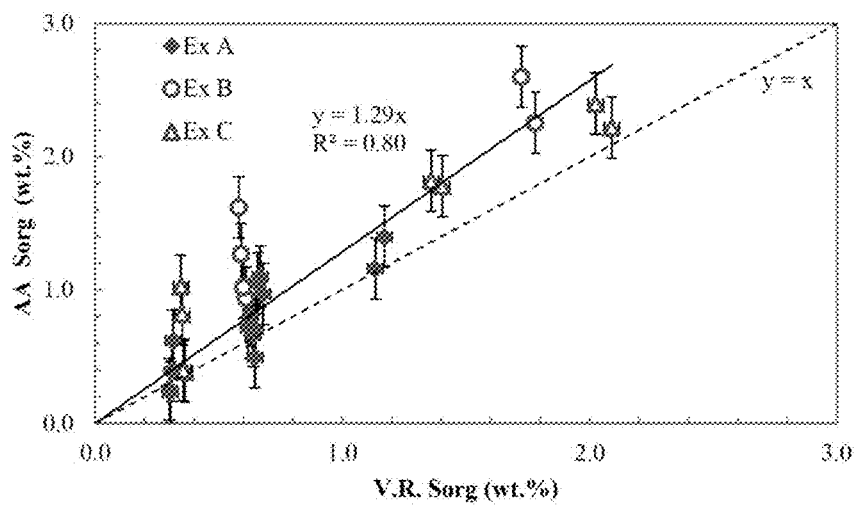
FIG. 5e presents the organic sulfur content determined by use of a process according to the prior art for samples of various type, as a function of the actual organic sulfur content of these samples.

FIGS. 5d and 5e present respectively the evolution of the pyritic sulfur (AA $S_{pyrit}$) and organic sulfur (AA $S_{org}$) contents obtained by means of the process according to the prior art, as a function of the reference contents, respectively, of pyritic sulfur (VR $S_{pyrit}$) and of organic sulfur (VR $S_{org}$) for each of the mixtures of the EXA type (that is to say 14 "pyrite+Orbagnous" mixturex), for each of the mixtures of the EXB type (that is to say 6 "pyrite+Phosphoria" mixtures) and for each of the mixtures of the EXC type (that is to say 8 "pyrite+Limagne" mixtures).

A poorer correlation between the pyritic sulfur and organic sulfur contents determined using the process according to the prior art and the reference contents of pyritic sulfur and of organic sulfur can be observed in FIGS. 5d and 5e.

Thus, the present invention makes it possible to significantly improve the precision of the determination of the pyritic sulfur content contained in a sedimentary rock sample, and consequently the precision of the determination of the organic sulfur content contained in a sedimentary rock sample.

TABLE 1a

| Formations<br>Ages<br>Country | Orbagnous<br>Kimmeridgian<br>France | | | | Phosphoria<br>Permian<br>United States | |
|---|---|---|---|---|---|---|
| Samples | O-9m | O-9ka | O-9cb | O-9ca | P-55 | P-43 |
| OI (mg $CO_2$/g TOC) | 40.0 | 25.6 | 11.6 | 24.0 | 127.5 | 61.3 |
| HI (mg HC/g TOC) | 964.6 | 969.6 | 811.8 | 887.5 | 134.5 | 372.5 |
| Mineral carbon content (wt. %) | 11.2 | 10.8 | 0.8 | 10.7 | 0.3 | 0.4 |
| Weight of rock (mg) | 60 ± 0.02 | 60 ± 0.02 | 60 ± 0.02 | 30 ± 0.02 | 60 ± 0.02 | 30 ± 0.02 |
| Organic sulfur content (wt. %) | 0.3 ± 0.03 | 0.7 ± 0.03 | 0.7 ± 0.03 | 1.21 ± 0.03 | 0.6 ± 0.03 | 1.8 ± 0.03 |
| Weight of pyrite (mg) | 1; 2; 3;<br>4 ± 0.02 | 1; 2; 3;<br>4 ± 0.02 | 1; 2; 3;<br>4 ± 0.02 | 1;<br>2 ± 0.02 | 1; 2; 3;<br>4 ± 0.02 | 1;<br>2 ± 0.02 |
| Pyritic sulfur content (wt. %) | 53 ± 2 | 53 ± 2 | 53 ± 2 | 53 ± 2 | 53 ± 2 | 53 ± 2 |

TABLE 1b

| Formations<br>Ages<br>Country | Limagne<br>Oligocene-Eocene<br>France | | |
|---|---|---|---|
| Samples | L-S18-2 | L-S02-5 | L-S05-2 |
| OI (mg $CO_2$/g TOC) | 39.0 | 31.5 | 30.5 |
| HI (mg HC/g TOC) | 549.0 | 660.0 | 691.5 |
| Mineral carbon content (wt. %) | 0.1 | 0.2 | 0.2 |
| Weight of rock (mg) | 60 ± 0.02 | 30 ± 0.02 | 30 ± 0.02 |
| Organic sulfur content (wt. %) | 0.4 ± 0.03 | 2.2 ± 0.03 | 1.5 ± 0.03 |
| Weight of pyrite (mg) | 1; 2; 3; 4 ± 0.02 | 1; 2 ± 0.02 | 1; 2 ± 0.02 |
| Pyritic sulfur content (wt. %) | 2 | 53 ± 2 | 53 ± 2 |

The invention claimed is:

1. A process for quantifying the pyritic sulfur in a sedimentary rock sample, in which at least the following steps are applied:
   A. the sample is heated in an inert atmosphere, between a first temperature of between 80° C. and 320° C. and a second temperature of between 600° C. and 700° C., while following a first temperature sequence, and an amount of hydrocarbon-based compounds, an amount of CO and an amount of $CO_2$ released during the first temperature sequence are continuously measured;
   B. at least one portion of the effluents resulting from the heating of the sample in an inert atmosphere is continuously oxidized, an amount of $SO_2$ released by the oxidation of the effluents as a function of the time of the heating in an inert atmosphere is continuously measured, and at least one pyrolysis pyritic sulfur content $S_{Pyrol}^{Pyrit}$ is determined from the amount of $SO_2$;
   C. the residue of the sample resulting from the heating in an inert atmosphere is heated in an oxidizing atmosphere between a third temperature of between 280° C. and 320° C. and a fourth temperature of greater than or equal to 800° C., while following a second temperature sequence, and an amount of CO and an amount of $CO_2$ released during the second temperature sequence are continuously measured;

wherein at least one pyritic sulfur content $S^{Pyrit}$ contained in the sample is determined on the basis of a formula:

$$S^{Pyrit} = S^{Pyrit}_{pyrol} * \frac{\left(1 + \frac{\beta}{1-\beta} + \frac{\gamma}{1-\gamma}\right)}{\alpha}$$

wherein $\alpha$ is a parameter representing a proportion of the pyrolysis pyritic sulfur relative to the total sulfur, $\beta$ is a parameter representing an effect of the mineral matrix on the proportion, and $\gamma$ is a parameter representing an effect of the organic matrix on the proportion, the values of the parameters $\alpha$ and $\beta$ being predetermined, and the parameter $\gamma$ being determined from a formula:

$\gamma = f(OI, HI)$ wherein $f$ is a function of at least one oxygen index OI and of a hydrogen index HI, the hydrogen index HI being a function at least of the amount of hydrocarbon-based compounds measured during the heating in an inert atmosphere and the amounts of CO and of $CO_2$ measured during the first and second temperature sequences, and the oxygen index OI being a function at least of the amounts of CO and of $CO_2$ measured during the first and second temperature sequences.

2. A process according to claim 1, in which the function $f$ is a linear combination of the oxygen index OI and of the hydrogen index HI which is expressed according to a formula: $\gamma = a*OI + b*HI + c$, wherein a, b and c are predetermined constants.

3. A process according to claim 2, in which the constant a is between 0.28 and 0.46.

4. A process according to claim 2, in which the constant b is between −0.007 and −0.005.

5. A process according to claim 2, in which the constant c is between 4.99 and 6.49.

6. A process according to claim 1, in which the hydrogen index HI is determined according to a formula $$HI = \frac{100*S2}{RC+PC},$$

wherein

S2 is an amount of hydrocarbon-based compounds which are cracked during the first temperature sequence, S2 being determined from the amount of hydrocarbon-based compounds released during the heating in an inert atmosphere;

TOC is a total organic carbon content of the sample which is written in the form TOC(wt %)=PC+RC, wherein PC is an organic carbon content from pyrolysis of the sample determined from the measurements of CO and $CO_2$ released during the first temperature sequence, and wherein RC is a residual organic carbon content of the sample determined from the measurements of CO and of $CO_2$ released during the second temperature sequence.

7. A process according to claim 1, in which the oxygen index OI is determined according to a formula:

$$OI = \left[\frac{100*S3CO_2}{TOC}\right],$$

wherein:

S3CO2 is an amount of $CO_2$ measured between the first temperature of the first temperature sequence and a first intermediate temperature of the first temperature sequence of between 350° C. and 450° C., and preferentially equals 400° C.; and TOC is a total organic carbon content of the sample and is written TOC(wt %)=PC+RC, wherein PC is an organic carbon content from pyrolysis of the sample determined from the measurements of CO and $CO_2$ released during the first temperature sequence, and wherein RC is a residual organic carbon content of the sample determined from the measurements of CO and of $CO_2$ released during the second temperature sequence.

8. A process according to claim 6, in which the pyrolysis organic carbon content PC of the sample is determined according to a formula:

$$PC(\text{wt \%}) = [Q*0.083] + \left[\left(S3CO + \frac{1}{2}S3'CO\right) * \frac{12}{280}\right] + \left[S3CO_2 * \frac{12}{440}\right],$$

with

S3CO2 is an amount of $CO_2$ measured between the first temperature of the first temperature sequence and a first intermediate temperature of the first temperature sequence of between 350° C. and 450° C.;

S3'CO is an amount of CO measured between the first temperature of the first temperature sequence and a second intermediate temperature of the first temperature sequence of between 500 and 600° C.;

S3'CO is an amount of CO measured between the second intermediate temperature of the first temperature sequence and the second temperature of the first temperature sequence.

9. A process according to claim 6, in which the residual organic carbon content RC of the sample is determined according to a formula:

$$RC(\text{wt \%}) = \left[S4CO_2 * \frac{12}{440}\right] + \left[S4CO * \frac{12}{280}\right],$$

wherein S4CO and S4CO2 correspond respectively to an amount of CO and of $CO_2$ measured between the third temperature of the second temperature sequence and an intermediate temperature of the second temperature sequence of between 600° C. and 700° C.

10. A process according to claim 1, in which the sample is a reservoir rock, and in which the first temperature is between 100° C. and 200° C.

11. A process according to claim 1, in which the sample is a source rock or immature shale, and in which the first temperature is between 280° C. and 320° C.

12. A process according to claim 1, in which the sample is a gas-bearing or oil-bearing shale, and in which the first temperature is between 80° C. and 120° C.

13. A process according to claim 1, in which the parameter $\alpha$ is between 0.40 and 0.46.

14. A process according to claim 1, in which the rock sample is a clay, and for which the parameter β is between 0.04 and 0.7.

15. A process according to claim 1, in which the rock sample is a marl, and for which the parameter β is between 0.7 and 0.9.

16. A process according to claim 1, in which the rock sample is a limestone, and for which the parameter β is between 0.85 and 0.97.

17. A process according to claim 1, in which, in addition, an amount of SO2 released during the second temperature sequence is measured, at least one pyrolysis sulfur content $S_{Pyrol}$ is determined from the amount of SO2 measured during the first temperature sequence and an oxidation sulfur content $S_{Oxy}$ is determined from the amount of SO2 measured during the second temperature sequence, and an organic sulfur content $S^{Org}$ is determined from at least the pyritic sulfur content $S^{Pyrit}$, from the pyrolysis sulfur content $S_{Pyrol}$ and from the oxidation sulfur content $S_{Oxy}$.

18. A process according to claim 17, in which the fourth temperature is between 800° C. and 900° C., and in which an organic sulfur content $S^{Org}$ is determined according to the formula: $S_{Org}=S_{Pyrol}+S_{Oxy}-S^{Pyrit}$.

19. A process according to one claim 17, in which the fourth temperature is greater than 1150° C., and is preferentially less than 1250° C., and in which a sulfate sulfur content $S_{Oxy}^{Sulfa}$ is also determined from the amount of SO2 measured during the second temperature sequence, and an organic sulfur content is deduced therefrom according to the formula: $S^{Org}=S_{Pyrol}+S_{Oxy}-S_{Pyrit}-S_{Oxy}^{Sulfa}$.

* * * * *